United States Patent [19]

Bova et al.

[11] Patent Number: 5,027,818
[45] Date of Patent: Jul. 2, 1991

[54] DOSIMETRIC TECHNIQUE FOR STEREOTACTIC RADIOSURGERY SAME

[75] Inventors: Frank J. Bova; William A. Friedman, both of Gainesville, Fla.

[73] Assignee: University of Florida, Gainesville, Fla.

[21] Appl. No.: 353,816

[22] Filed: May 18, 1989

Related U.S. Application Data

[63] Continuation-in-part of Ser. No. 128,273, Dec. 3, 1987, abandoned.

[51] Int. Cl.⁵ .............................................. A61B 6/00
[52] U.S. Cl. .................... 128/653.00 R; 364/413.14; 364/413.15; 364/413.16; 364/413.22; 378/65; 606/130
[58] Field of Search ................. 128/653 R, 654, 659; 378/65; 606/130; 364/413.14, 413.15, 413.16, 413.22, 413.26

[56] References Cited

U.S. PATENT DOCUMENTS

| | | |
|---|---|---|
| 2,181,620 | 11/1939 | Haupt . |
| 2,638,554 | 5/1953 | Bartow et al. . |
| 2,998,526 | 8/1961 | Green et al. . |
| 3,766,384 | 10/1973 | Anderson . |
| 3,777,124 | 12/1973 | Pavkovich . |
| 3,987,281 | 10/1976 | Hodes ................................... 378/65 |
| 3,991,310 | 11/1976 | Morrison ............................... 378/65 |
| 4,008,400 | 2/1977 | Brunnett et al. ................ 364/413.15 |
| 4,233,519 | 11/1980 | Coad . |
| 4,583,537 | 4/1986 | Derechinsky et al. . |
| 4,729,099 | 3/1988 | Iverson et al. .................. 364/413.26 |

FOREIGN PATENT DOCUMENTS

| | | |
|---|---|---|
| 0075831 | 4/1983 | European Pat. Off. . |
| 0083756 | 7/1983 | European Pat. Off. . |
| 88/05321 | 7/1988 | European Pat. Off. . |
| 2014151 | 12/1971 | Fed. Rep. of Germany . |
| 2337859 | 2/1975 | Fed. Rep. of Germany . |
| 2385374 | 3/1978 | France . |

OTHER PUBLICATIONS

*The Physics of Radiology*, Harold Elford Johns & John Robert Cunningham, Fourth Edition, pp. 385-388.
*The Physics of Radiation Therapy*, Faiz M. Khan, Ph.D., pp. 249-254.

Primary Examiner—Lee S. Cohen
Assistant Examiner—Krista M. Pfaffle
Attorney, Agent, or Firm—Kerkam, Stowell, Kondracki & Clarke

[57] ABSTRACT

Stereotactic radiosurgery is facilitated by a technique for computing the doses at various points within the patient's body. In particular, the doses are computed at a relatively high density of points within a fine dose grid and at a relatively low density of points within a coarse dose grid. In that fashion, the user can quickly obtain necessary information about the radiation dose distribution before implementation of a proposed treatment plan. An advantageous technique of locating the intersection between the radiation beam and the contour or other surface of the patient is also provided. The method is especially well suited for use with a particular structure which allows one to utilize relatively narrow beam widths as a result of great mechanical accuracy.

20 Claims, 19 Drawing Sheets

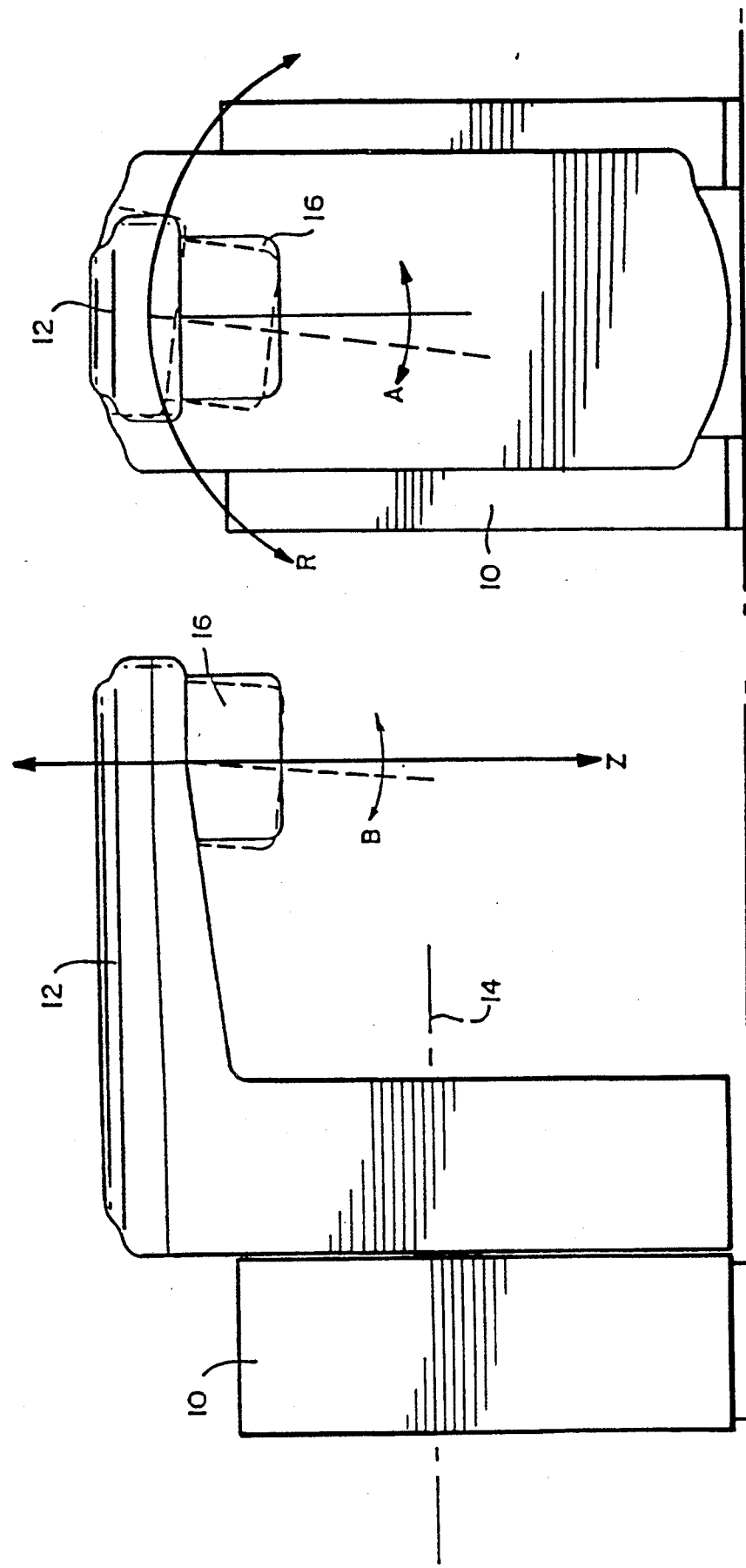

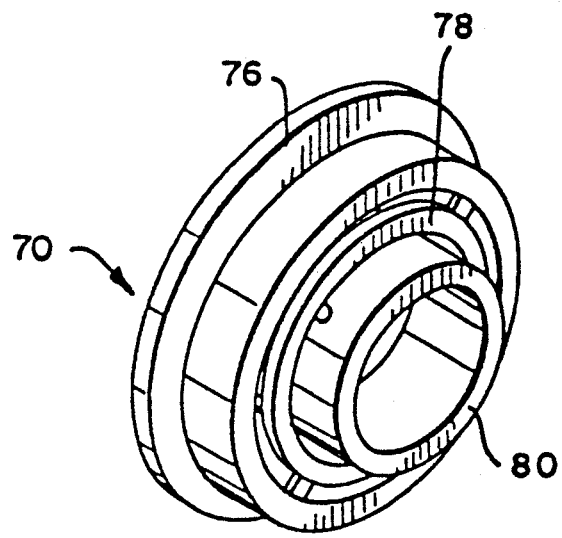
FIG. 8
FIG. 9
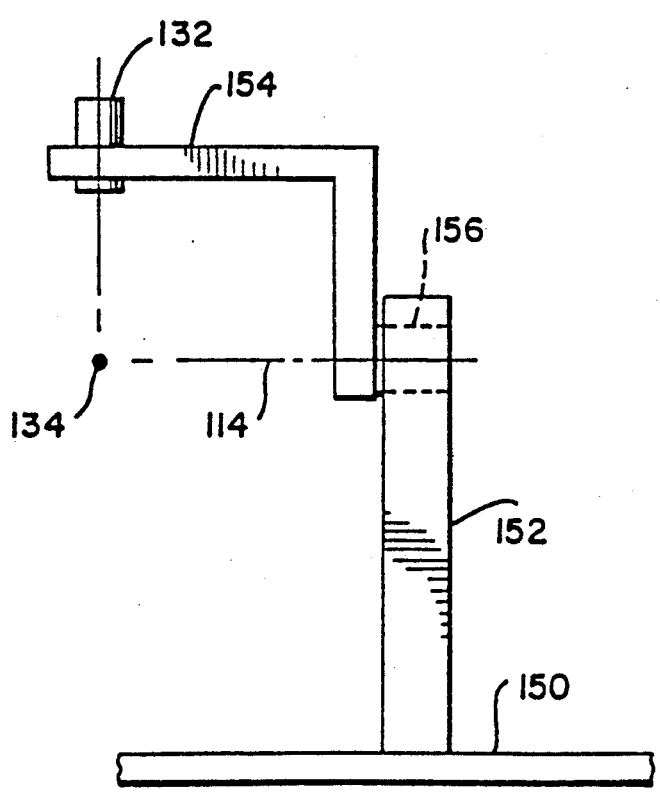
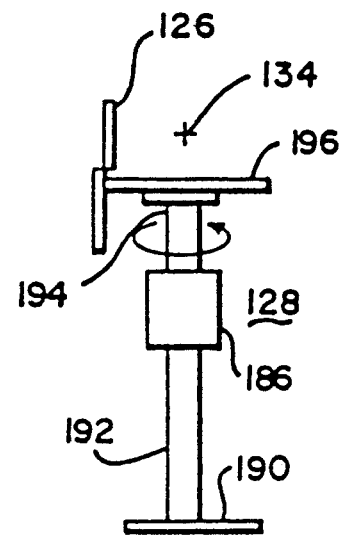
FIG. 10

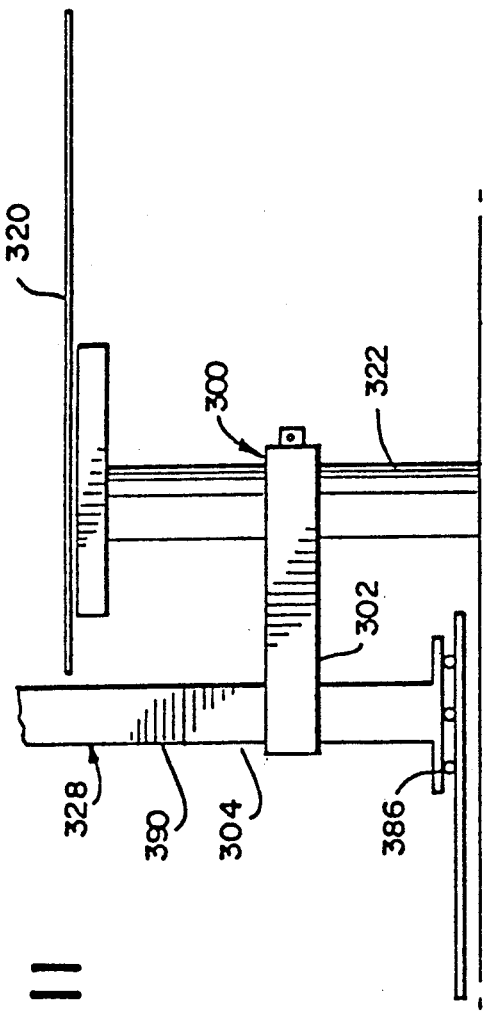
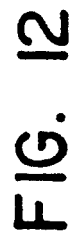
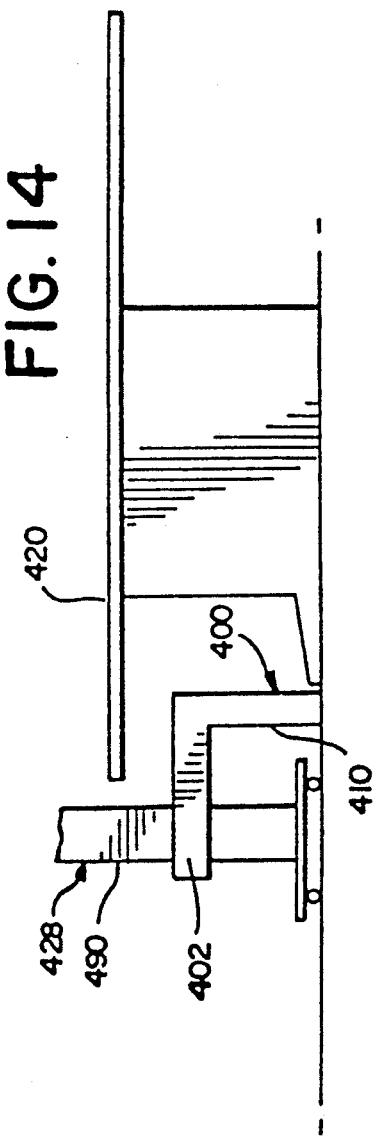
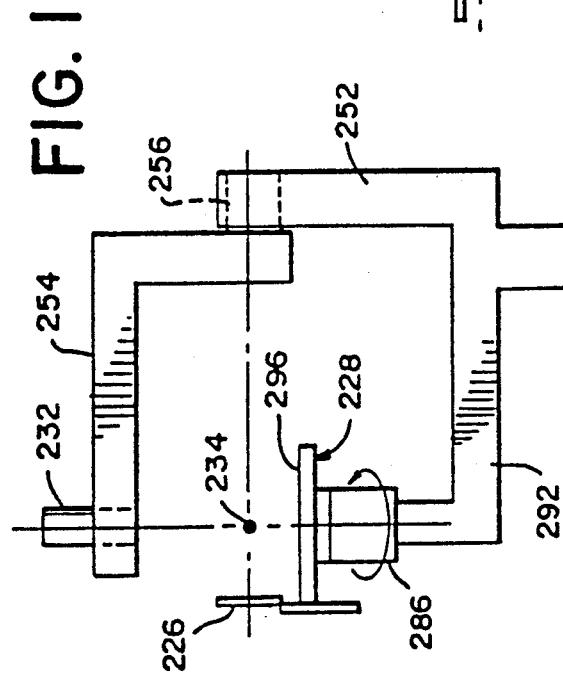
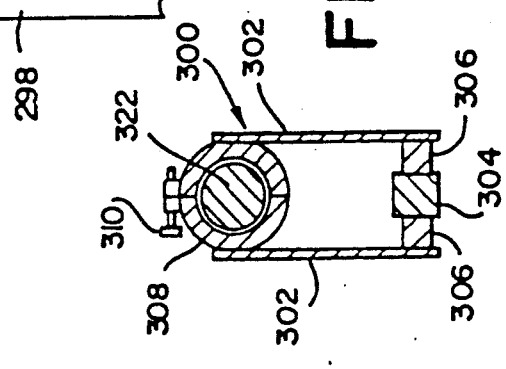

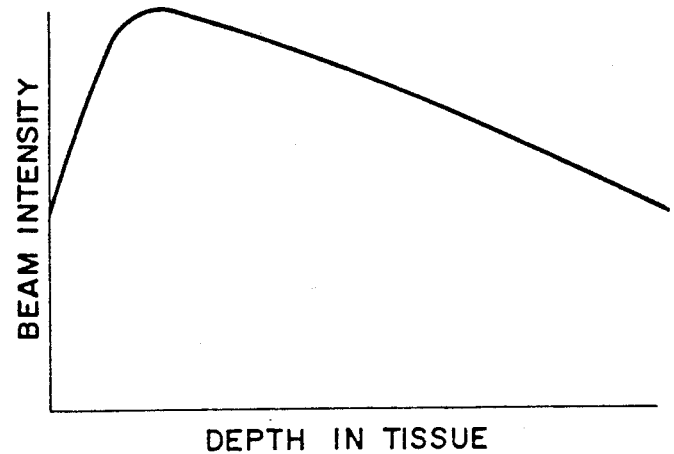
FIG. 20A
FIG. 20B
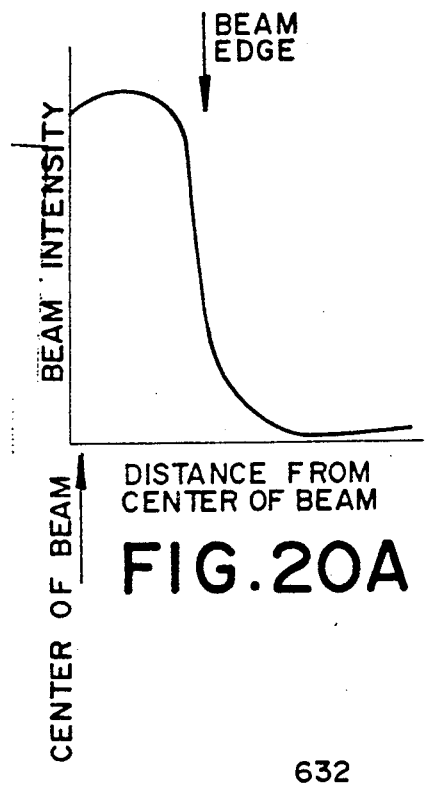
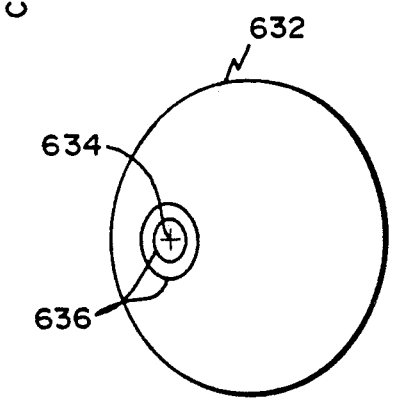
FIG. 25
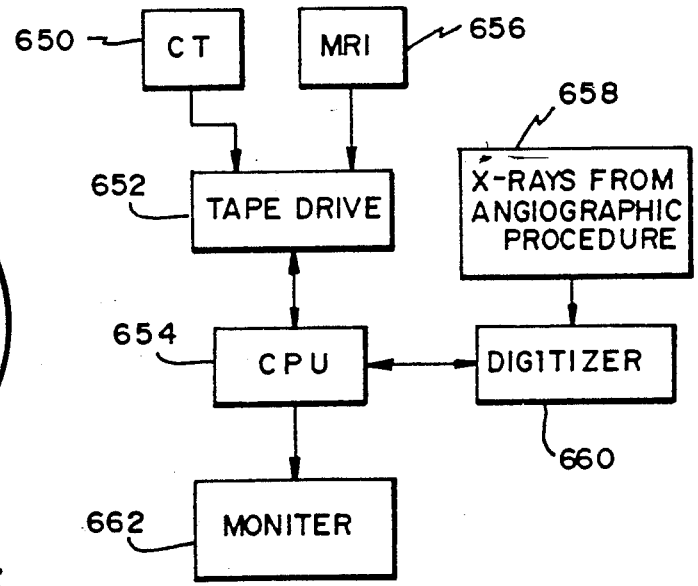
FIG. 27

DOSIMETRIC TECHNIQUE FOR STEREOTACTIC RADIOSURGERY SAME

CROSS-REFERENCE TO RELATED APPLICATIONS

This application is a continuation-in-part (CIP) of International Application No. PCT/US 88/04 303 filed Dec. 2, 1988 designating the U.S., among other countries. That application will, in its U.S. stage, be a CIP of U.S. application 128,273 filed Dec. 3, 1987 and now abandoned. Both of those applications are incorporated by reference.

A portion of the disclosure of this patent document contains material subject to copyright protection. The copyright owner has no objection to facsimile reproduction by anyone of the patent document or the patent disclosure, as it appears in the Patent and Trademark Office patent file or records, but otherwise reserves all copyright rights whatsoever.

REFERENCE TO THE MICROFICHE APPENDIX

This application was filed with a computer program listing printout which has been submitted in the form of a "microfiche appendix". The microfiche appendix consists of four sheets of microfiche consisting of a total of 237 frames and is not a part of the printed patent.

BACKGROUND OF THE INVENTION

This invention relates generally to dosimetry for a radiosurgery system employing multiple beams of radiation focused onto a stereotactically localized target, and more particularly to a dosimetry technique which quickly provides useful data for planning patient treatment.

In 1951, Dr. Lars Leksell coined the term "radiosurgery", to describe the concept of focusing multiple beams of external radiation on a stereotactically localized intracranial target. After experimentation with standard X-ray treatment devices, proton beam, and linear accelerators, he and his collaborators developed a device which is called the GAMMA KNIFE (currently marketed by the Electra Corporation, Stockholm, Sweden). The device consists of a hemispheric array, currently containing 201 Cobalt-60 sources. The radiation from each of these sources is collimated and mechanically fixed, with great accuracy, on a focal point at the center of the hemisphere. When a patient has a suitable lesion for treatment (usually an intracranial arteriovenous malformation), it may be precisely localized with another device called a stereotactic frame. Using the stereotactic apparatus, the intracranial target is positioned at the focal point of the GAMMA KNIFE. Since each of the 201 radiation pathways is through a different area of the brain, the amount of radiation to normal brain tissue is minimal. At the focal point, however, a very sizable dose is delivered which can, in certain cases, lead to obliteration of the lesion. This radiosurgical treatment is, in some instances, a much safer treatment option than conventional surgical methods.

Several GAMMA KNIFE devices are currently being used worldwide for stereotactic radiosurgery and have been used to treat approximately 1500 patients. The results of treatment, as well as many technical issues, have been discussed in multiple publications. Several factors, however, have impeded the widespread usage of this device. First, the device costs about $2.2 Million Dollars, U.S. Second, the Nuclear Regulatory Commission has ruled that this device cannot be shipped loaded in the U.S.A. Consequently, loading must be done on site, necessitating the construction of a portable hot cell. Third, the half life of Cobalt-60 is 5.2 years, which requires reloading the machine, at great expense, every 5-10 years. Fourth, the dosimetry system currently marketed with the device is relatively crude, especially when utilized with more modern imaging modalities such as CT scan and MRI scan.

An alternative method for radiosurgery involves irradiation of intracranial targets with particle beams (i.e., proton or helium). In this instance, one does not rely solely on multiple cross-fired beams of radiation. A physical property of particle beams, called the "Bragg-peak effect", allows one to deliver the majority of the energy of a small number of beams (approximately 12) to a precisely predetermined depth. Multiple publications regarding particle irradiation of intracranial lesions (especially pituitary tumors and arteriovenous malformations) have appeared in the literature. The results have not generally been as good as those obtained with the GAMMA KNIFE. This may, however, be solely a consequence of patient selection criteria. Particle beam devices require the availability of a cyclotron. Only a few such high energy physics research facilities exist in the world.

A third current radiosurgical method uses a linear accelerator (LINAC) as the radiation source. As mentioned above, Leksell rejected the LINAC as mechanically inaccurate. More recently, groups from Europe have reported their methods for radiosurgery with LINAC devices. In the United States, researchers at the Peter Bent Brigham Hospital in Boston have developed a prototype LINAC system using highly sophisticated computer techniques to optimize dosimetry. Thus far, approximately 12 patients have been treated with good results. This LINAC system, however, suffers from certain mechanical inaccuracies which have limited its use. In addition, the computer dosimetry system employed is very time consuming, rendering the treatment program inefficient.

Currently, there is great interest in radiosurgery. Although the GAMMA KNIFE represents the "gold standard", its great expense and requirement for frequent replenishment of radiation sources have discouraged most potential users. The proton beam devices are never likely to be widely available because of the requirement for high-energy particle beam source (cyclotron). The linear accelerator offers an attractive alternative to such devices. However, a major disadvantage of known linear accelerator based systems is the need for time consuming (e.g., several hours) computer calculations for determining the radiation distributions.

Before subjecting a patient to stereotactic radiosurgery, the tumor or other target area within the patient must be localized. This may be accomplished by stereotactic angiography or by CT (computer tomography) localization. After the localization of the tumor or other target area, a CT localizer (or an NMR imaging system) should be used on the patient, even if the original localization was using stereotactic angiography. The data from the CT scan and the angiographic films, if any, should be transferred to a computer system used for calculating the dosage.

When applying radiation to a patient, it is important that the radiation be concentrated on the target area and minimized for the patient's healthy tissues. It is especially important that the radiation be minimized on certain critical structures. For example, if using radiation treatment on a patient's brain, it may be important that the radiation dosage applied to the patient's optic nerves is minimized.

Before a physician applies the radiation to the patient, the physician may decide on two or more arcs which will be used for applying the radiation to the patient. In particular, the physician decides upon the plane in which the radiation beam will be applied in an arc to the patient's target area. The localization data and the proposed treatment arcs are input into a dosimetric computer system. That computer system generates a value for the radiation at each point in a grid extending throughout the patient's skull (assuming that the radiation is for the treatment of a target area within the brain). It is this process that is very time consuming and may require over four hours of computer time. Specifically, the process usually generates the value of the radiation dose at over 250,000 points within the patient's skull. After the doctor has received the radiation distributions from the computer, the doctor may decide that one or more critical structures is receiving too much radiation. Alternately, the doctor may decide that the target area is not receiving sufficient radiation. At any rate, the doctor may be required to revise the arcs through which the radiation source will travel in order to apply radiation to the tumor. It would then be necessary to repeat the very time consuming process of recalculating the radiation distribution.

Some prior dosimetric computer systems have been designed in which the radiation distribution may be calculated and shown or supplied for a smaller volume than the complete volume of the patient's skull. These type of systems require that one repeatedly indicate the area or volume for which the radiation distribution is desired. Although this may give faster results than the process giving the complete radiation distribution, the results are somewhat incomplete unless the doctor repeatedly selects numerous areas or zones for which the radiation distribution is requested. Each radiation distribution that is generated shows only a portion of the plane of view illustrating the radiation distributed within the patient.

The time-consuming nature of prior dosimetric systems is at least partly due to the generally used technique for calculating where the beam goes into the patient's skull. Specifically, the patient's skull may be simulated by thousands (often hundreds of thousands) of tiles and the usual "tiling" technique uses a series of simultaneous equations in order to calculate where the beam of radiation enters the patient's skull.

A further reason for the time-consuming nature of prior dosimetric procedures is that the resolution must be sufficiently high to give adequate details of the radiation distribution. In other words, the points at which the radiation dosages are given must be sufficiently close together that the doctor will have enough information to make proper decisions. On the other hand, this requirement for high resolution causes one to use so many data points that the calculations will, on most computers, take a tremendous amount of time.

A further reason for the time-consuming nature of previous dosimetric techniques is that such techniques require radiation distribution calculations based upon relatively complex mathematical models. The models require that the entrance width of the beam be taken into account because the width of the beam is generally large compared to the curvature of the patient's skull. In other words, the center of the radiation beam might be perpendicular to the patient's skull, but the beam is sufficiently wide compared to the curvature of the patient's skull that the edge of the beam is entering the patient's skull at a significantly different angle than at the beam center. Since the portion of the beam entering at the edge has a significantly different angle than the center of the beam, prior systems have generally taken into account this edge effect. This increases the complexity of the calculations. A further reason for the complexity of calculating the radiation distribution is that prior techniques usually require calculation of the primary radiation and the scattered radiation. The primary radiation is radiation which reaches a point inside the target volume with few interactions with the overlying material, whereas the scattered radiation is the radiation distribution resulting from the interaction of the primary radiation with the overlying structures or materials away from the primary path. The scattered radiation does not proceed along the same directional path as the primary radiation or the beam.

A further disadvantage of prior dosimetric systems is that they lack flexibility in terms of providing requested data.

OBJECTS AND SUMMARY OF THE INVENTION

A primary object of the present invention is to provide a new and improved dosimetric technique for stereotactic radiosurgery.

A more specific object of the present invention is to provide an improved dosimetric technique which avoids or minimizes the problems associated with the prior dosimetric techniques as discussed above.

The present invention uses localization in order to determine the target area (such as a tumor or other area to be treated) within a patient. An imaging system is used on the patient, such as a CT scanner, angiography, or NMR system. Using the localization data obtained, an operator supplies a computer with a series of arcs corresponding to the manner of applying radiation to the target area within the patient. The arcs are input into a computer system which has been programmed to perform the present dosimetric analysis. The computer system will very quickly generate data for the doctor showing the radiation distribution within the patient from the proposed arcs.

Advantageously, the present invention avoids many of the calculations of the prior dosimetric systems by providing a different resolution within a zone close to the isocenter (i.e., a location within the target zone at which the radiation will be most concentrated) and a zone removed from the isocenter. In other words, there might be a grid in the high-resolution zone where the radiation distribution is calculated every one millimeter, whereas the radiation distribution would be calculated every five millimeters in a grid outside of the high resolution zone or area. Accordingly, the number of data points may be significantly reduced without lowering the useful information supplied to the doctor since the low-resolution zone or area corresponds to locations where the radiation distribution changes only very slowly.

Another advantageous technique of the present invention is to use a thin beam of radiation such that the scattered radiation may be ignored and the beam may be modeled as though it strikes the patient's skull at a single point. In other words, the beam may be sufficiently thin compared to the curvature of the patient's skull so that one may ignore the edge effects discussed above.

A further advantageous feature of the present invention is that one avoids the tiling technique to determine where the beam enters the patient's skull. Instead of performing the simultaneous equations, the present dosimetric technique uses a computer to graphically proceed along the radiation beam from the target area towards the source of the radiation. The computer can recognize whether the beam is inside the patient's skull or has just transversed into the outside of the patient's skull.

A further significant feature of the present invention is that it allows the user to arbitrarily select key planes for display of the radiation distribution.

BRIEF DESCRIPTION OF THE DRAWINGS

The above and other features of the present invention will be more readily understood when the following description is considered in conjunction with the accompanying drawings wherein like parts have the same number throughout and in which:

FIGS. 1 and 2 are a side elevation view and an end elevation view, respectively, of conventional linear accelerator apparatus which may be employed for stereotactic radiosurgery, the figures illustrating possible misalignments of a radiation-emitting head of the apparatus;

FIG. 8 is a perspective view illustrating conceptually a preferred form of a gimbal bearing;

FIG. 9 shows an alternate arrangement for supporting a collimator;

FIG. 10 shows an alternate arrangement for supporting a floorstand;

FIG. 11 shows a further alternative arrangement for supporting both the collimator and a floorstand by way of a common support;

FIG. 12 shows a side view of an arrangement for linking rotation of a floorstand to rotation of a treatment table;

FIG. 13 shows a cross-section view of the connection between the floorstand and treatment table of FIG. 12;

FIG. 14 shows a side view of an alternate arrangement for linking a floorstand to a table;

FIGS. 20A and 20B show beam intensity distributions respectively as a function of the distance from the center of a beam and the depth in tissue of the beam;

FIG. 25 shows how the present invention includes radiation dose information on the display of a portion of the patient's body;

FIG. 27 shows a simplified schematic of a system for implementing the present technique.

DETAILED DESCRIPTION

Figure 3:
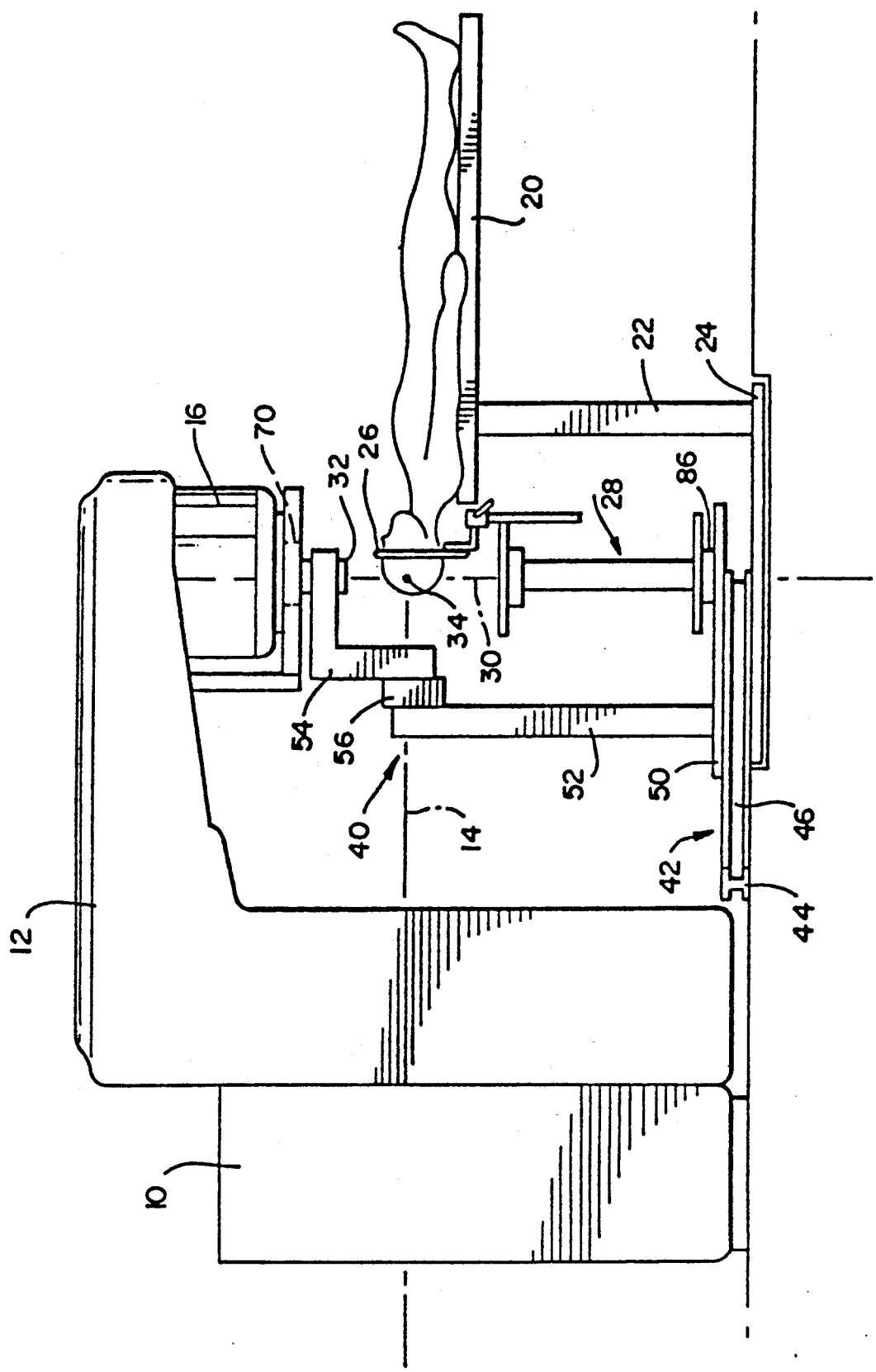
FIGS. 3 and 4 are a side elevation view and a top view, respectively, of stereotactic radiosurgery apparatus useful in implementing the invention.

The process of the present invention is especially well adapted for use in conjunction with a specific linear accelerator structure which will be initially described herein. However, it should be noted that the present dosimetric technique has more general application.

FIGS. 1 and 2 illustrate a conventional LINAC device which comprises a fixed base 10 and an L-shaped gantry 12 which is rotatable with respect to the base about a horizontal axis 14. The gantry carries a radiation-emitting head 16, and rotation of the gantry causes the head to sweep through an arc R located in a substantially vertical plane which is perpendicular to the horizontal axis. The dotted lines in the figures indicate potential misalignments caused by mechanical inaccuracies or sag of the gantry in any of the directions indicated in the FIGS. as A, B or z. These misalignments result in misfocusing of the radiation from the head 16 and are intolerable in radiosurgery, for the reasons noted hereinafter.

In order to best understand the invention, the three principle components of a stereotactic radiosurgery procedure will first be explained. These components are localization, dose computation and optimization, and execution of treatment. The ultimate accuracy of the procedure is dependent on each of these components.

The first component in the procedure involves the localization of the tumor. This is accomplished by one of two means. Currently, the method of choice is through stereotactic angiography. The procedure begins with the stereotactic ring being fitted to the patient. An angiographic localizing device is then attached to the ring. This device is known and consists of four sets of fiducial alignment markers. Two sets of these markers project onto each of two orthogonal angiographic x-rays. By location of the fiducial points and the target on each x-ray, the precise, x, y, z coordinates of the target (to an accuracy of 1 mm) relative to the stereotactic ring can be derived. While this part of the procedure allows the coordinates of the target relative to the localization ring to the determined, more anatomical information is needed for dosimetric analysis.

The next step replaces the angiographic localizing device with another localizer specially designed for localization in computer tomography. This is the standard BRW CT Localizer. The patient is aligned in the CT gantry and contiguous 5 mm slices, beginning at the level of the localization ring and advancing superiorly past the top of the patient's skull, are obtained. If the target volume can be identified in the computerized tomography image, then the x, y, z coordinates of the target volume are again calculated. (This can provide a double check of the x, y, z coordinates relative to the stereotactic ring.) If not, then the target obtained from the angiographic procedure can then be superimposed onto the CT scan data.

With the digitally encoded data from the CT scan and the two angiographic films, the data may be then transferred to a dosimetry computer system. The CT scan provides three dimensional anatomical information of the patient allowing a solid patient model to be constructed. The coordinates of the target volume from the angiogram and the CT scan data are then merged.

Computation and Dose Optimization: In order for the high single fractions of radiation to be delivered to the target volume, a technique to concentrate the radiation at the target while spreading out the radiation to lesser concentrations throughout the normal tissues must be utilized. Moving the radiation source through multiple arcs achieves this objective. It is important for the radiotherapist and neurosurgeon to be able to examine the consequence of each portion of the arc. The computer system which computes the dosimetry must have the ability to display each arc segment. In the routine stereotactic procedure, it is anticipated that four arcs, three at 100 degrees and one at 240 degrees, will be utilized. The computer must allow the CT scan to be reformatted in each of these arc planes (relative to the patient's skull) so that each individual arc's dose distribution can be examined. If any particular arc results in an extensive dose to a critical structure, the therapist can alter the arc parameters to avoid the anatomical area of concern. The dosimetry system discussed in detail below will allow dose optimization through operator control. For as yet undeveloped more sophisticated versions, the operator will identify the target region and the areas where dose should be minimized. The computer will then, through use of an optimization algorithm, design the treatment which best concentrates the radiation over the tumor volume while minimizing the dose to normal tissues. The spacing between arcs, the size of the collimator, and the variation in arc length and weight will be parameters used in the optimization.

The method necessary for dose computation and optimization using a CT scan is complicated by the high resolution necessary in the procedure. The stereotactic targets can be identified to plus and minus a millimeter. The treatment portals can range anywhere from 1 to 3 cm in diameter. The spatial coordinates of the computational grid, in the area of the target, must be in the 1 mm range. However, there is little need for 1 mm accuracy outside about a 5 cm radius of the target itself. A 0.5 grid is adequate in this region. By working with both the 1 mm and 5 mm grids, the number of computation points at which a dose must be evaluated for the complex arcs can be vastly reduced.

Once the acceptable treatment scheme has been derived, the coordinates of the isocenter (focal point of the radiation), the collimator size, and the arc parameters are then transferred to the operator of the linear accelerator.

Figure 4A:
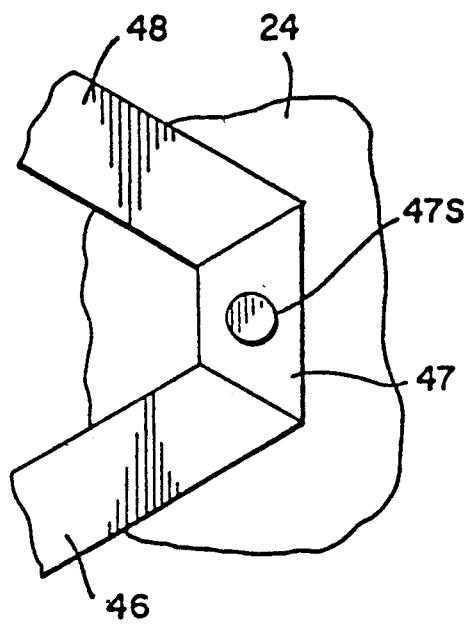
FIG. 4A is a top view showing parts of a floorstand support arrangement.
Figure 4B:
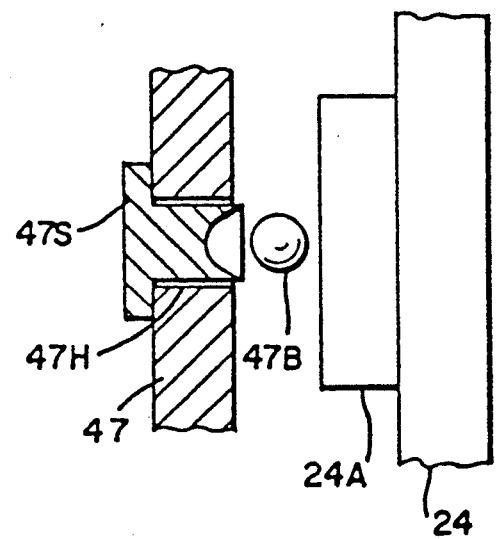
FIG. 4B shows a side exploded view with some parts in cross-section of parts of FIG. 4A.
Figure 4:
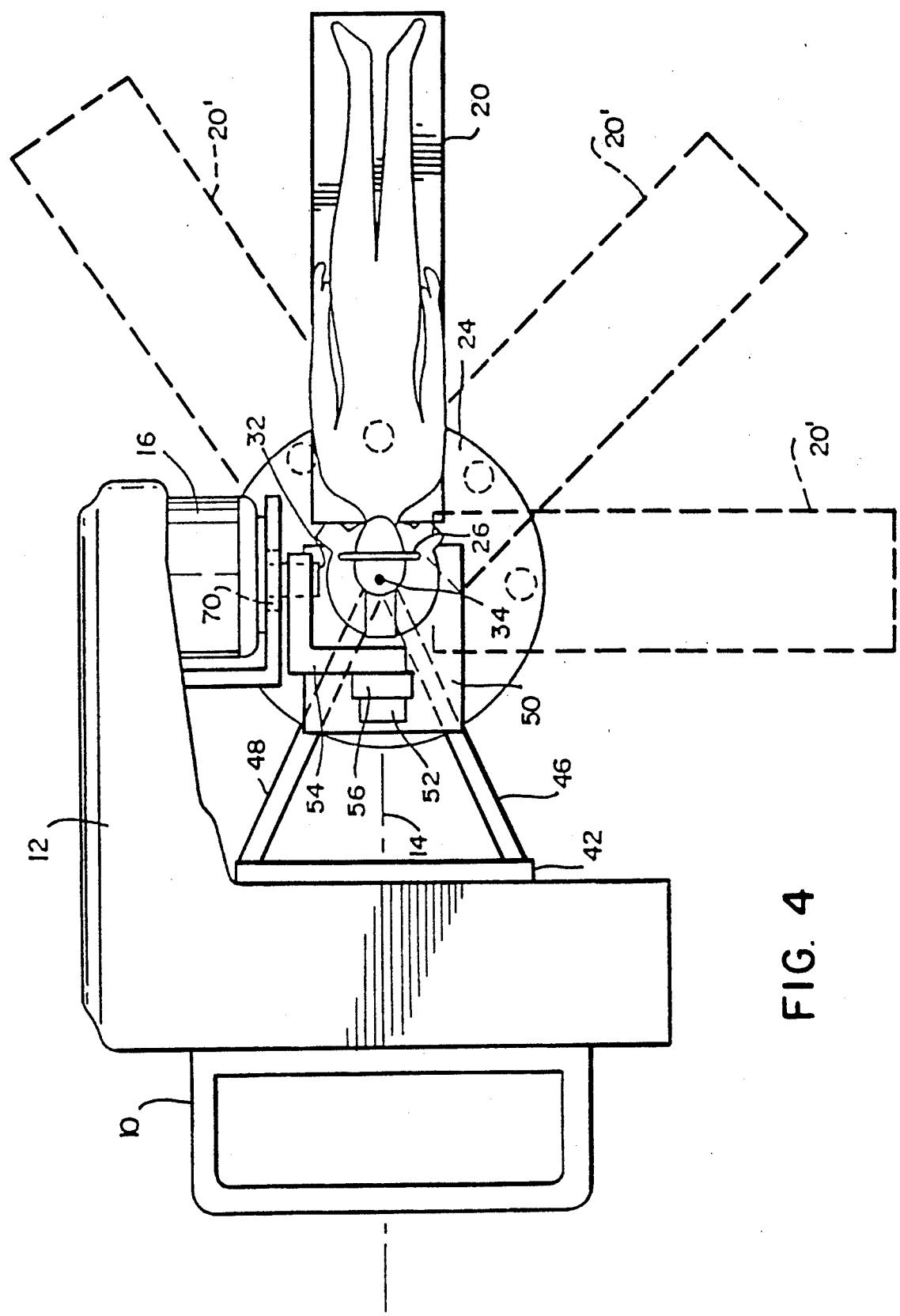

FIGS. 3 and 4 illustrate the stereotactic treatment setup. As shown, a patient is placed on a treatment table 20 which is supported by a member 22 on a rotating plate 24 positioned in the floor. The patient's head is immobilized by a stereotactic ring 26 which is connected to a BRW stereotactic floorstand 28 which has been modified in accordance with the invention (as will be explained shortly) so that the patient's head is at a predetermined location with respect to the radiation-emitting head 16 of the LINAC. As shown in FIG. 4, rotating plate 24 may be rotated, to position the table at different locations 20' as indicated by the dotted lines. Gantry 12 of the LINAC may be rotated about base 10 to swing treatment head 16 in an arc located in a vertical plane indicated by the dotted line 30 in FIG. 3. The radiation from head 16 is collimated by a collimator 32 and is confined to the vertical plane 30 in which the treatment head moves. FIG. 4 shows the gantry 12 swung over to one side such that the radiation enters the left side of the patient's head, and FIG. 3 shows the gantry in an upright position such that the radiation enters through the forehead of the patient. Collimator 32 focuses the radiation at an isocenter or center point 34 corresponding to the intersection of the horizontal axis 14 of rotation of the gantry and vertical plane 30. Center point 34 corresponds to the origin of the arc through which the treatment head 16 swings. Rotating plate 24 rotates about a vertical axis which coincides with vertical plane 30. Accordingly, as gantry 12 is swung through an arc the radiation of head 16 passes through different portions of the patient's head and is concentrated at center point 34 for all rotational positions of rotating plate 24.

Prior to treatment of the patient, a test treatment procedure is first run. A phantom pointer allows placement of a stainless steel ball as a phantom target on the modified stereotactic floorstand 28 in accordance with a known test procedure and an appropriate collimator placed into the stereotactic dose delivery apparatus (radiation-emitting head 16). A trial arc is then made to assess the mechanical precision and accuracy of placement of the moving treatment head, and the overall accuracy of the location procedure is tested using radiation and x-ray film in known fashion. If this is successful, patient treatment is executed.

As previously noted, mechanical inaccuracies and sag in the gantry as it is rotated through its arc can cause deviations from the nominal origin of the arc (center of rotation) and, thus, deviations in the focal point of the radiation from the desired center point 34. Attempting to deliver a dose of radiation to a spherical volume with an accuracy of plus or minus 1 mm requires that the LINAC have tolerances which are much more stringent than that. Conventional LINAC's have a gantry isocentric accuracy of 2 mm, and patient support rotation has an accuracy of 2 mm. It is therefore possible for a target placed at the isocenter 34 to find itself 4 mm from the center of the radiation beam after gantry and table rotation. This is clearly unacceptable. If small treatment targets are to be attempted, these potential isocentric inaccuracies must be eliminated. The described system accomplishes this by employing a guiding and stabilizing structure 40 which rotates in the vertical plane 30 of the gantry rotation and confines the movement of collimator 32 to a precise arc with no more than 0.1 mm misalignment. Moreover, the apparatus reduces the rotational inaccuracy of the treatment table to a maximum misalignment of 0.1 mm, as will be described shortly. By reducing the allowable treatment table and gantry misalignments by a factor of 10 from the normal inaccuracies, the apparatus enables a dose of radiation to be delivered to a target within plus or minus 1 mm. The guiding and support structure 40 and the stereotactic floorstand 28 of the invention which accomplish this are shown in FIGS. 3 and 4 and in somewhat more detail in FIGS. 5 and 6.

Figures 5, 5A:
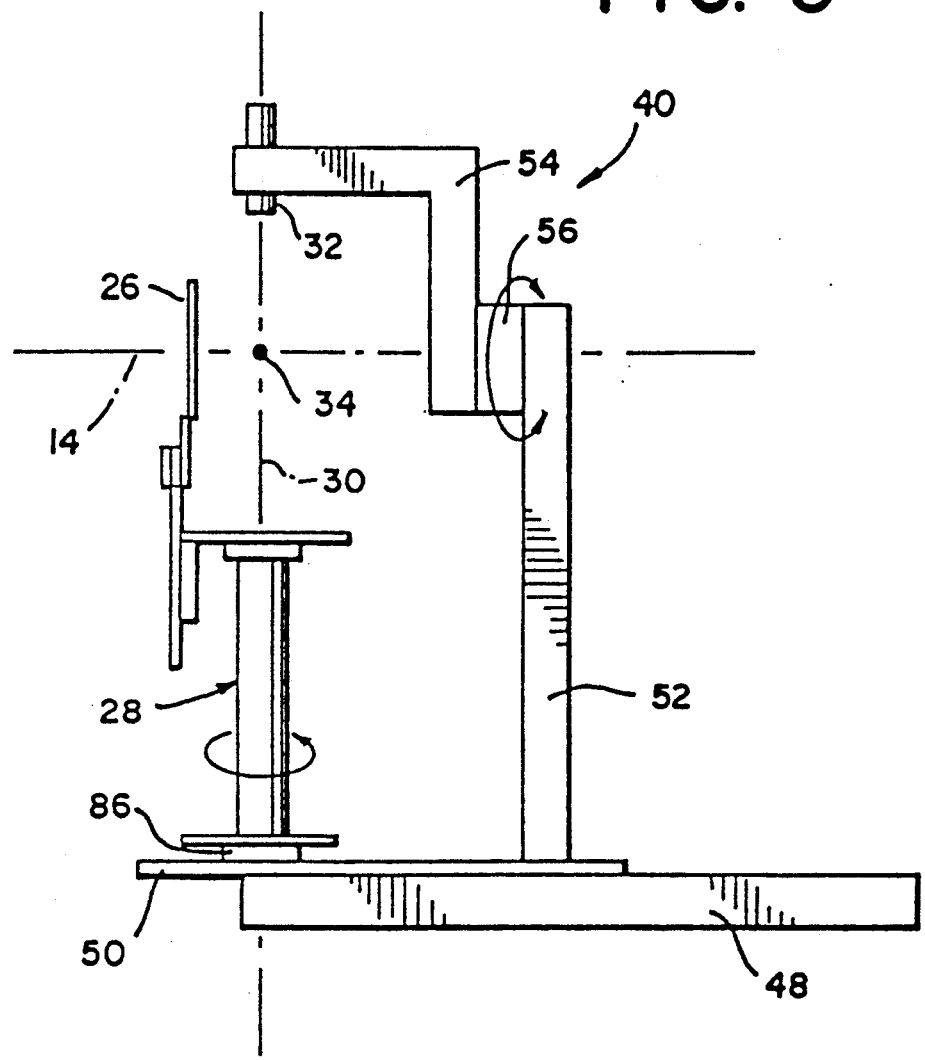
FIGS. 5 and 6 are a side elevation view and a top view, respectively, of guiding structure.
FIG. 5A is a top exploded view of parts from FIG. 5.
Figure 6:
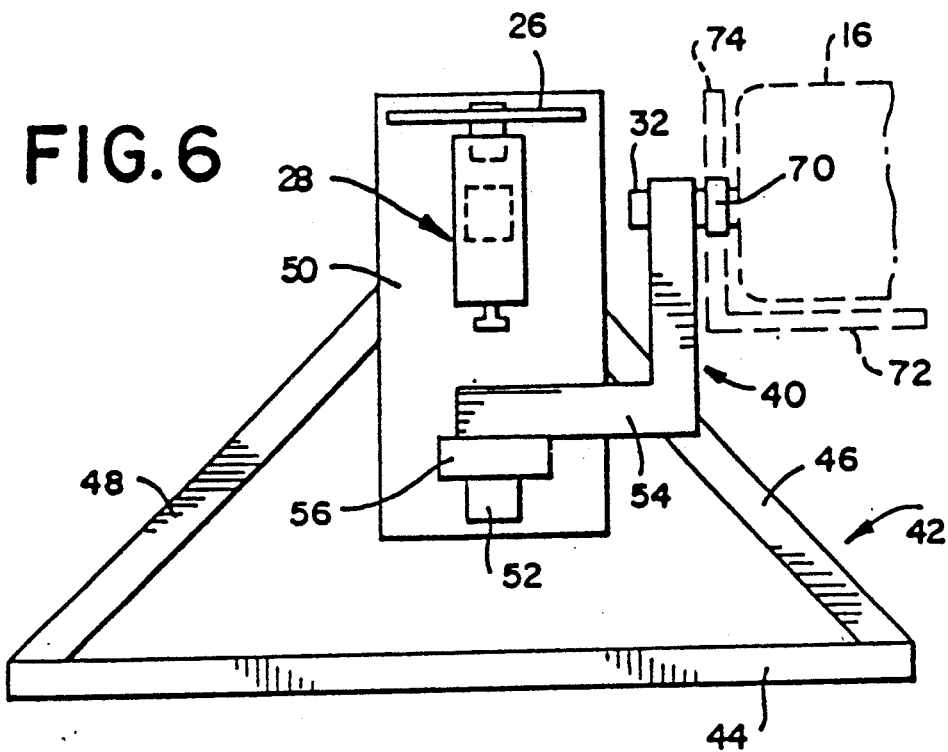

Referring to these figures, the apparatus employs an A-frame supporting structure 42 which may be constructed of H-beams. One beam, such as 44 may be connected to the floor adjacent to the gantry such that the two arms 46 and 48 extend over rotating plate 24 (See FIG. 3, 48 is behind 46 in the view of FIG. 3, but is seen in FIGS. 4, 5 and 6) and are spaced therefrom to enable the plate to rotate. A generally rectangular plate 50, as of aluminum, may be supported on the frame as shown. Plate 50 supports the rotating and guiding structure 40 and the floorstand 28.

As shown in FIG. 4A and FIG. 4B, arms 46 and 48 are connected by member 47, disposed below plate 50 (plate 50 not shown in FIGS. 4A and 4B). To prevent the plate 50 and floorstand mounted thereon from sagging from the cantilever extensions of arms 46 and 48, the plate 50 is supported by bearing 47B which is captured between screw 47S and plate 24A which is fixed to plate 24. As plate 24 moves, bearing 47B allows such movement but supports the plate 50.

As shown in the FIGS., the guiding and supporting structure 40 may comprise a first substantially vertical support member connected to plate 50, and a second angled support member 54 rotatably connected to the upper end of support member 52 by a main arcing bearing 56 such that the center of rotation of support member 54 coincides with horizontal axis 14 about which the gantry rotates. The main arcing bearing 56 comprises a high precision bearing, which may take the form illustrated in FIG. 7. As shown, the bearing may comprise a first fixed plate 60, as of steel, which rotatably supports a center plate 62 having a hub 64. Center plate 62 is captured in three orthogonal directions by rolling bearings 66 and is machined to a flatness and concentric accuracy which allows no more than 0.03 mm in variation as it rotates. Plate 60 may be connected to the vertical support member 52, and hub 64 may be connected to support member 54.

As shown in the FIGS., collimator 32 is connected to the horizontal (in FIGS. 3 and 5) arm of support member 54. As shown in FIG. 5A, member 54 may include two pieces 54F and 54S with complimentary holes to clamp collimator 32 when bolted together by bolt 54B extending through hole 54H. Collimator 32, in turn, may be coupled to head 16 of the LINAC through the use of a gimbal-type bearing 70, such as shown in FIG. 8. As shown in FIG. 8, the gimbal bearing may comprise an outer ring 76, an intermediate ring 78 pivotally connected to the outer ring, and an inner ring 80 pivotally connected to the intermediate ring 78. Ring 80 constitutes a slip collar which snugly and slidingly receives the collimator 32.

Figure 3A:
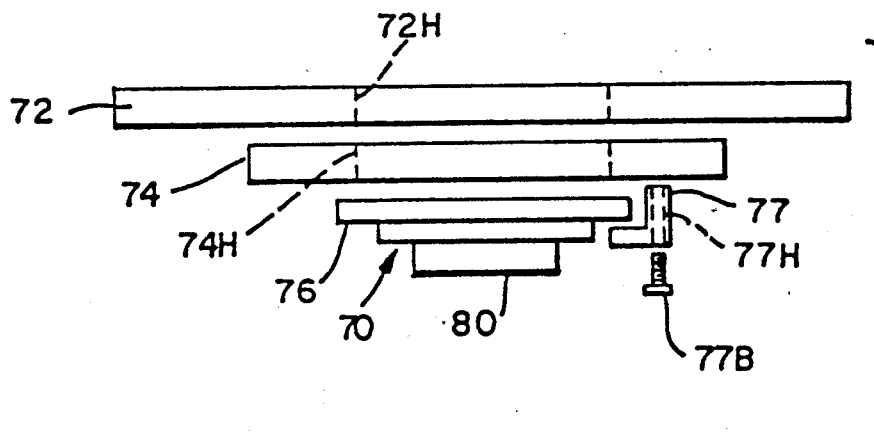
FIG. 3A is a side exploded view of a linking arrangement for linking a collimator to a radiation-emitting head.

With reference to FIG. 3A, gimbal 70 would be clamped to plate 74 by several circumferentially spaced L-shaped members 77 (only one shown) with bolt 77B extending through hole 77H into a hole (not shown) in plate 74. Plate 74, which has a circular hole 74H, is positioned relative to plate 72 by positioning pins (not shown) on plate 74 cooperating with positioning holes (not shown) on plate 72 and is bolted (bolts now shown) to plate 72. Plate 72 has hole 72H which, like hole 74H, allows it to accommodate a collimator (not shown in FIG. 3A) placed within ring 80. The plate 72 would be mounted to the radiation head by positioning pins and holes and bolts. The collimator slip ring 80 could be moved slightly by loosening the members 77 and re-tightening them after gimbal 70 and its ring 80 are repositioned.

As gantry 12 rotates, support and guiding structure 40 serves to guide the collimator through a very precise and accurate arc having a center of rotation at center point 34. Gimbal bearing 70 allows the head of the LINAC to pull the collimator through the arc as the gantry rotates, but removes all torques on the collimator. Thus, any misalignments or sag of the gantry in any direction will not be transmitted to the collimator and will not result in any forces on it. Thus, support and guiding structure 40 compensates for any misalignments in the rotation of the gantry by ensuring that the movement of the collimator 32 is precisely controlled. As a result, the radiation from head 16 is precisely focused at center point 34.

An alternative to gimbal 70 could be a ball and socket (not shown) with the socket secured to the radiation head 16 and the ball having a cylindrical hole to accommodate the collimator in slip ring fashion and avoid putting torque on the collimator.

Figure 7:
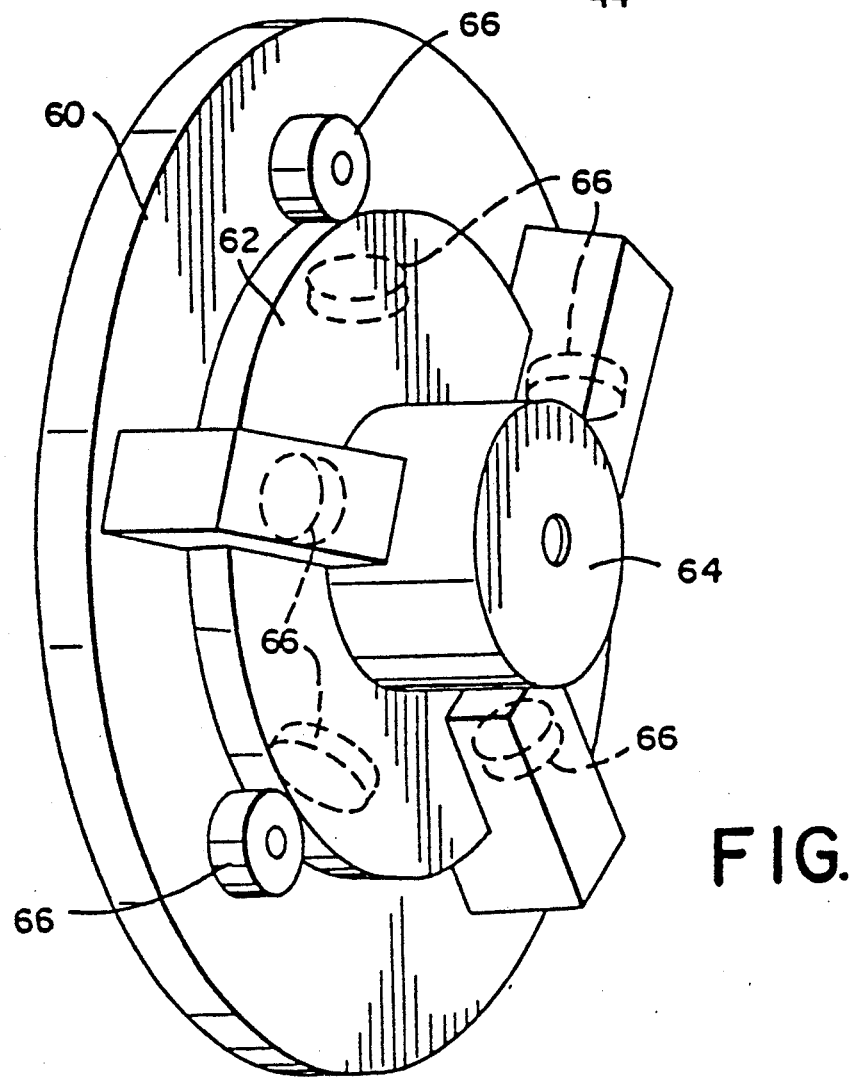
FIG. 7 is a perspective view illustrating conceptually a preferred form of a main arcing bearing.

Floorstand 28 is also rotatably mounted on plate 50 by a bearing 86, which may be similar to the main arcing bearing of FIG. 7. The floorstand is precisely located such that its axis of rotation is vertical and lies in plane 30. The axis of rotation of the floorstand intersects center point 34. Bearing 86 of the floorstand is also machined to a flatness and concentric accuracy which allows no more than 0.03 mm in variation as it rotates. Accordingly, the floorstand compensates for any rotational inaccuracies in rotating plate 24 and ensures that the treatment point in the patient's head precisely coincides with isocenter 34 for all rotational positions of the table. Unlike prior floorstands which have been directly mounted to a plate such as 24, the use of bearing 86 allows floorstand 28 to avoid inaccuracies from the rotation of plate 24. Floorstand 28 is independently anchored from table 20 (i.e., floorstand 28 is not fixed relative to table 20 and plate 24).

Once alignment of the guiding and support structure 40 and the rotating floorstand 28 with respect to plate 50 have been achieved, all components are doweled and pinned in position to maintain the alignment. The floorplate may then be mounted on the H-beam structure. This arrangement provides a mounting system which can be easily fitted and removed from the LINAC such that when the LINAC is not being used for a stereotactic procedure, the LINAC is returned to its unmodified state.

With reference now to FIG. 9, an alternate arrangement for mounting a collimator is shown. For ease of illustration, the simplified side view of FIG. 9 only includes elements which are different from the structures previously discussed with respect to FIGS. 3-8.

The components of the structure of FIG. 9 are labeled in the 100 series with the same last two digits as the corresponding component, if any, of the previously discussed embodiment. A support member 152 is fixed to a plate 150 and is used to maintain the accuracy of rotation of collimator 132 about a gantry axis 114 (which axis is horizontal for the preferred embodiment). The collimator 132 functions in the same way as the previously discussed collimator 32 and would be coupled to a radiation head such as 16 of FIG. 3 by way of a mechanical linking means such as the gimbal structure previously discussed with respect to FIG. 3. However, since the linkage between the collimator 132 and such a radiation head would be identical to that shown in FIG. 3 and the related and earlier discussed FIGS., these features are not shown in FIG. 9. FIG. 9 is different than the previously discussed first embodiment in that the collimator 132 is mounted to the support member 152 by way of a support member 154 using an internal taper bearing 156 as opposed to the external type bearing 56 in the earlier discussed embodiment. Such taper bearings are well known and need not be discussed in detail, but it should briefly be noted that they are known bearing structures capable of very precise bearing arrangements.

FIG. 10 shows an alternate floorstand 128 (which might also be used with the structure of FIG. 9). The floorstand 128 has a fixed base 190 with a fixed shaft or member 192 extending up therefrom. A bearing system 186 allows rotation of a rotatable shaft 194 relative to the fixed shaft 192. A platform 196 is mounted on the top of the shaft 194 and a stereotactic ring 126 is mounted thereon. As with the earlier embodiment, the axis of rotation corresponding to the central axis of shaft 194 would be coaxial to the axis of rotation of a treatment table such as 20 of FIG. 3 and FIG. 4. This axis of rotation corresponding to the central axis of shaft 194 might be considered as a patient axis since the patient rotates about that axis upon movement of the treatment table 20 and rotation of the rotatable part of floorstand 128.

FIG. 11 shows an alternate construction wherein the precision bearing arrangement for a collimator 232 and a floorstand 228 are commonly mounted to a fixed member 298. The member 298, only a portion of which is shown, would be fixed to a base (not shown) in similar fashion to the fixing of member 52 in FIG. 3. Extending up from member 298 is a member or portion 252 which is rotatably connected to the collimator 232 by way of a support arm 254 and an internal taper bearing 256. A portion or member 292 connects a tapered bearing 286 to the floorstand 228 including platform 296 and stereotactic ring 226. The arrangement of FIG. 11 provides for highly precise rotation of a patient's head or other bodily part by way of the stereotactic floorstand portion 228 and highly accurate rotation of the collimator 232. The use of the precision tapered bearings 256 and 286 and the other elements of the structure of FIG. 11 would of course be used in connection with a treatment table and radiation-emitting head and other structures as shown in FIG. 3. For ease of illustration, FIG. 11, as well as the FIGS. 9 and 10, do not show portions of the system which are identical to the structures of FIGS. 3-8. In other words, the collimator 232 would be linked to the radiation head by way of a gimbal arrangement as previously discussed and the floorstand 228 would rotate in connection with rotation of a table 20 and about a common axis with such a table as discussed above with respect to FIGS. 3-8.

With reference now to FIG. 12, an arrangement for linking the movement between the treatment table 20 and the floorstand 28 will be shown. The structure of FIG. 12 would be identical to that shown previously with respect to FIG. 3-8 and only a portion is shown in FIG. 12 for convenience. Additionally however, FIG. 12 includes a linking means 300. As shown in FIG. 12 the linking means 300 is a mechanical structure including an arm 302 extending from the member 322 to a member 304 corresponding to the shaft of floorstand 328.

Considering FIG. 12 in conjunction with FIG. 13, the structure of floorstand linking means 300 is shown to include two of the arms 302 which are welded or otherwise fixed to a locking collar 308 using a bolt 310 to lock around the shaft 22 corresponding to the treatment table 20. The collar 308 might be hinged opposite bolt 310 or alternately could simply be compressed against its resilience by tightening bolt 310. The two arms 302 extend out and grip the member 304 which extends up as part of the stereotactic floorstand 328. Two pressure pads 306 grip the member 304 such that the member 304 rotates by way of bearings 86 upon rotation of the table 320. However, because of the linkage by way of the pressure pads 306, the precision bearings 86 provide very precise positioning of the floorstand 328 while minimizing any transmission of inaccuracies from the treatment table 320. The pressure pads 306 allow slight relative movements between the treatment table 320 and the floorstand 28.

FIG. 14 shows an alternate linking arrangement 400 which might be used to link rotation of a treatment table 420 having a toe bearing system. The linking means 400 includes a vertical shaft 410 which might be a single shaft or two parallel members such as the arms 302 in FIG. 13. In either case, the member 410 is fixed at its lower end to a plate which rotates with the table 420. The linkage arrangement 400 includes two arms 402 (only one of which is visible in FIG. 14). The two arms 402 are parallel and would have pressure pads similar to those shown at 306 of FIG. 13 such that the shaft 490 of floorstand 428 would rotate upon rotation of the table 420, but quite importantly would not incorporate the positional inaccuracies of the rotation of table 420.

It will be readily appreciated that the mechanical linking means 300 and 400 of FIGS. 12-14 could be used to link rotation of the floorstands shown in FIGS. 10 and 11 to rotation of a corresponding table.

Another significant advantage of the apparatus is that aside from the increased isocentric accuracy which it provides, it enables independent evaluation of each of the various degrees of freedom of movement required for the procedure. The rotation of the floorstand can be separately evaluated from the guiding and support structure of the collimator, and, similarly, the movements of the guiding and support structure may be separately evaluated from those of the floorstand. Moreover, the alignment of the gimbal bearing system can be evaluated separately from the movement of either of the other two rotational bearing systems. This affords a simpler and more efficient quality control of the entire system, and easily accommodates other radiographic verifications which may be required. The apparatus described above may be used in conjunction with a software package which will be described hereafter. The software package includes angiographic localization with computed tomographic localization and external beam treatment planning into a single package. This package allows the user to not only perform each exam, but enables the user to progress from each stage of the stereotactic radiosurgery procedure to the next with automatic transfer of all critical data. Because the data is passed from one program to the next, errors which might otherwise result from manual data reentry are avoided. It should be noted that the package advantageously provides for user inspection and approval of data such that the user may exclude data which is questionable or erroneous.

Angiographic localization may be used for intracranial vascular targets which can best be visualized with the use of contrast. A localization procedure uses the BRW (Browning-Roberts-Wells) angiographic localizer and based upon previously known equations. The overall software package, including the procedure or program for angiographic localization, uses windows of the type recently incorporated into various software systems in order to give the user greater flexibility and speed. The angiographic localization program, which is called ANGIOLOC, uses icons and windows which are part of the Sunview Pixrect package (Sun Microsystems).

Although the specifics of the angiographic localization are not necessary to the present invention, an outline of the program function is given in the appendix hereto and the program itself is also presented in the appendix hereto.

Computed tomography localization may be used for identifying the target in certain cases. For these cases, a program which allows the user to localize the target based upon a series of CT slices has been developed and is named CTPROG. That program, for which an outline of the program function is given in the appendix and the program itself is included in the appendix, provides extensive use of pop-up menus and pop-up windows. These features allow the user to quickly move through the localization procedure with a great amount of flexibility. Since the present invention is not directed to the specifics of the localization program, it should simply be noted that more details of the program may be found in the appendix. This and the other programs include various subparts which are included in the appendix. The programs are in the C language.

The ability to have all of the imaging modalities used in the overall present procedure in the same coordinate system is required. As previously noted, the BRW angiographic localizer is used, localization from sets of plane films is required. This allows the user to obtain the target in BRW space (a coordinate system which is relative to BRW localizing ring. For CT scanning, the BRW CT localizer has been used. The equations used to compute the BRW coordinates from the CT image data are known. Since many CT images are routinely needed in the practice of the overall procedure, a method for automatically processing the images has been developed and is specifically disclosed in the appendix attached hereto. This program has again been written with the use of windows and pop-up menus. As the present invention does not relate to the specifics of the tomographic processing, it should suffice to note that details are disclosed by the program in the appendix.

A key feature of the present invention is the procedure used to calculate the radiation dose applied to various parts of the patient. An important part of that procedure is the technique by which the present invention determines where a radiation beam enters the patient's body. The key features both relate to steps which are carried out by a program titled GAMMA which is attached as part of the appendix hereto and which is generally described in a separate of the appendix listing the functions in GAMMA. Since the GAMMA program includes specific features which are being claimed herein, this program will be discussed in more detail below.

Figure 15:
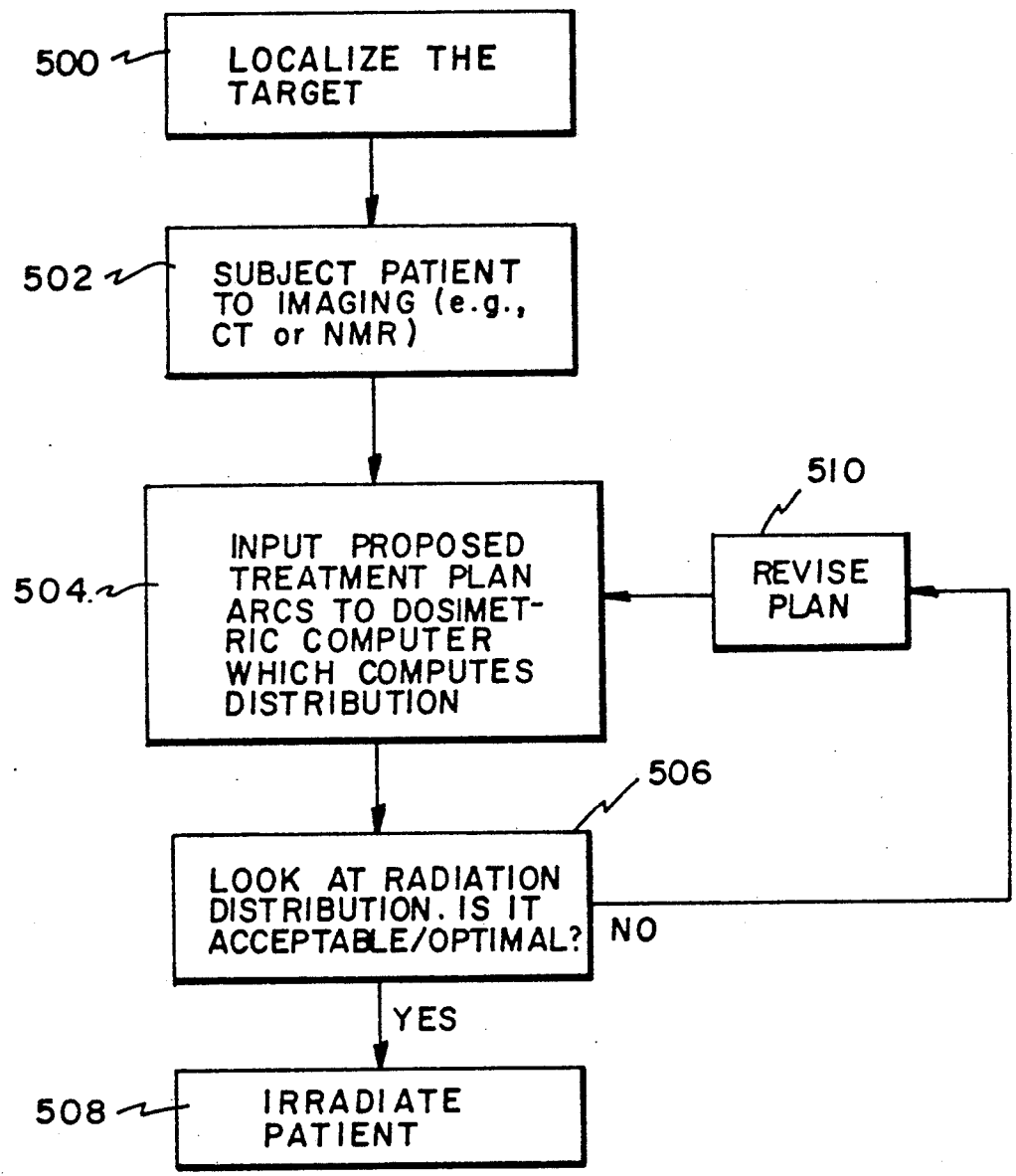
FIG. 15 shows a simplified flow chart of the overall patient treatment process according to the present invention.

Before discussing the operation of the GAMMA program in more detail, the overall procedure used for patient treatment will be shown with reference to FIG. 15. As shown in FIG. 15, the target, such as a tumor, is initially localized at block 500. The various localization techniques discussed above may be used. Next, the patient is subjected to imaging at block 502. The imaging, which may be CT, NMR, or other techniques, is used to generate x, y, and z coordinates of the target and adjacent portions of the patient, these coordinates being patient reference data.

Following the start of the imaging at block 502 (the imaging continues during subsequent steps), the user inputs a proposed treatment plan to a dosimetric computer. The dosimetric computer may be that identified above. At this stage, the user is proposing a plan of treatment for the patient corresponding to application of radiation through several arcs corresponding to rotation of the radiation head 16 about axis 14 and/or rotation of the patient table 20 about axis 30 (refer back to FIG. 3). The dosimetric computer computes the distribution, after which the user reviews the radiation distribution data at block 506. If the distribution is acceptable or optimal, the block 506 leads to block 508 whereupon the proposed treatment plan is implemented by using the apparatus described above in order to apply beams of radiation moving in the arcs to a patient. On the other hand, if the radiation distribution is not acceptable, or if the user would like to consider alternate radiation distributions, block 506 leads to block 510 whereat the user can revise the plan and input the revised plan at block 504.

A common problem with prior art procedures is that the computer takes so long to generate the distribution that it may effectively deny the doctor the opportunity to revise the plan. In contrast, the procedures discussed in more detail below for computing the radiation distribution will very quickly give a doctor the necessary information to consider whether revisions are desirable for the treatment plan.

Figure 16:
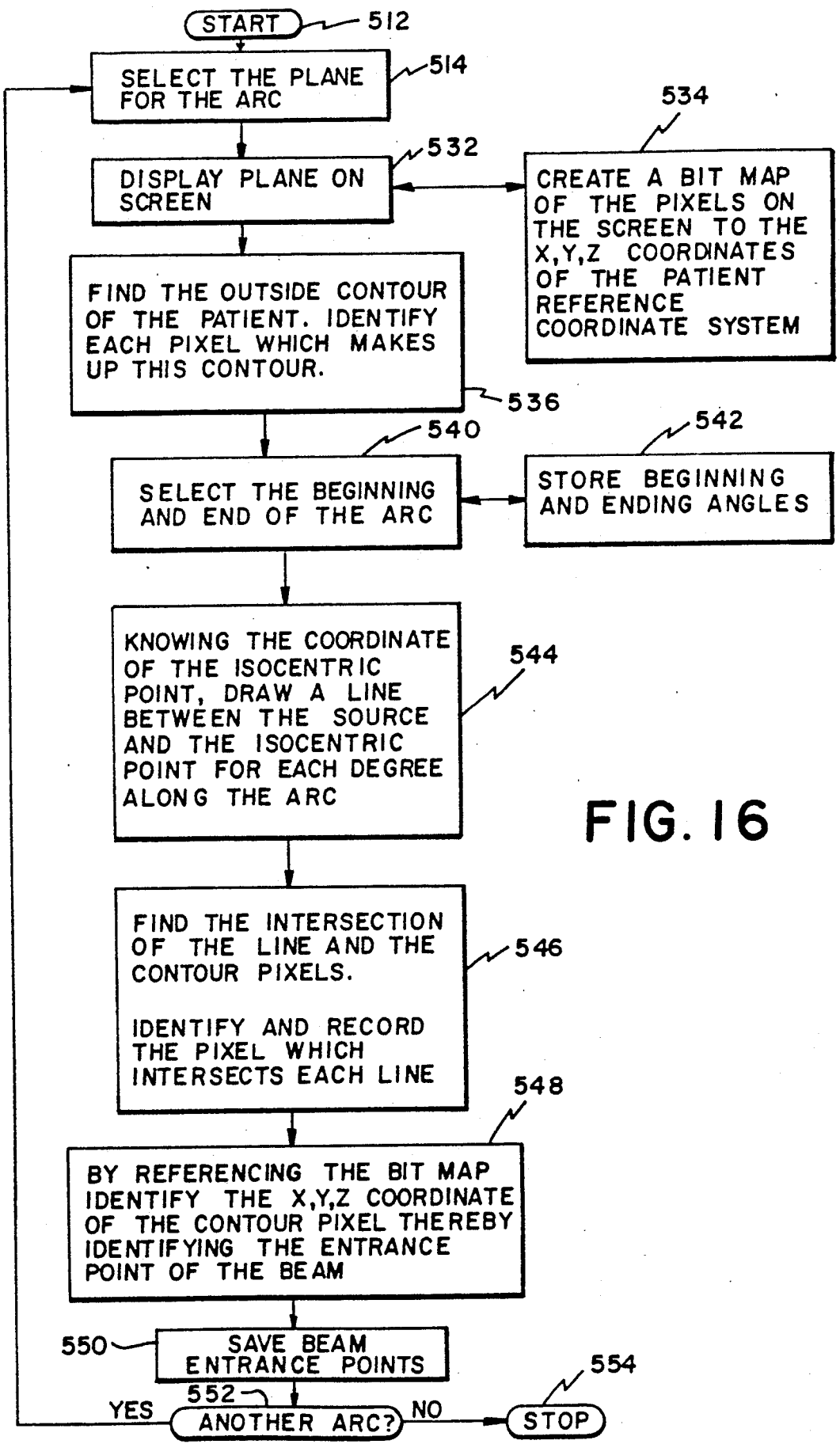
FIG. 16 shows a simplified flow chart of a method of setting a beam treatment arc and determining beam entrance points according to the present invention.

FIG. 16 shows a procedure for inputting the proposed treatment plan to a dosimetric computer and for determining the beam entrance points (i.e., where the radiation beams enter the patient's body). This procedure has been illustrated in FIG. 16 as a separate program but may either be a portion of the GAMMA program or could be subroutine of that program.

In the simplified flow chart of FIG. 16, the start block 512 leads to block 514 where the plane corresponding to an arc through which the beam is moved is entered into the computer.

Figure 17:
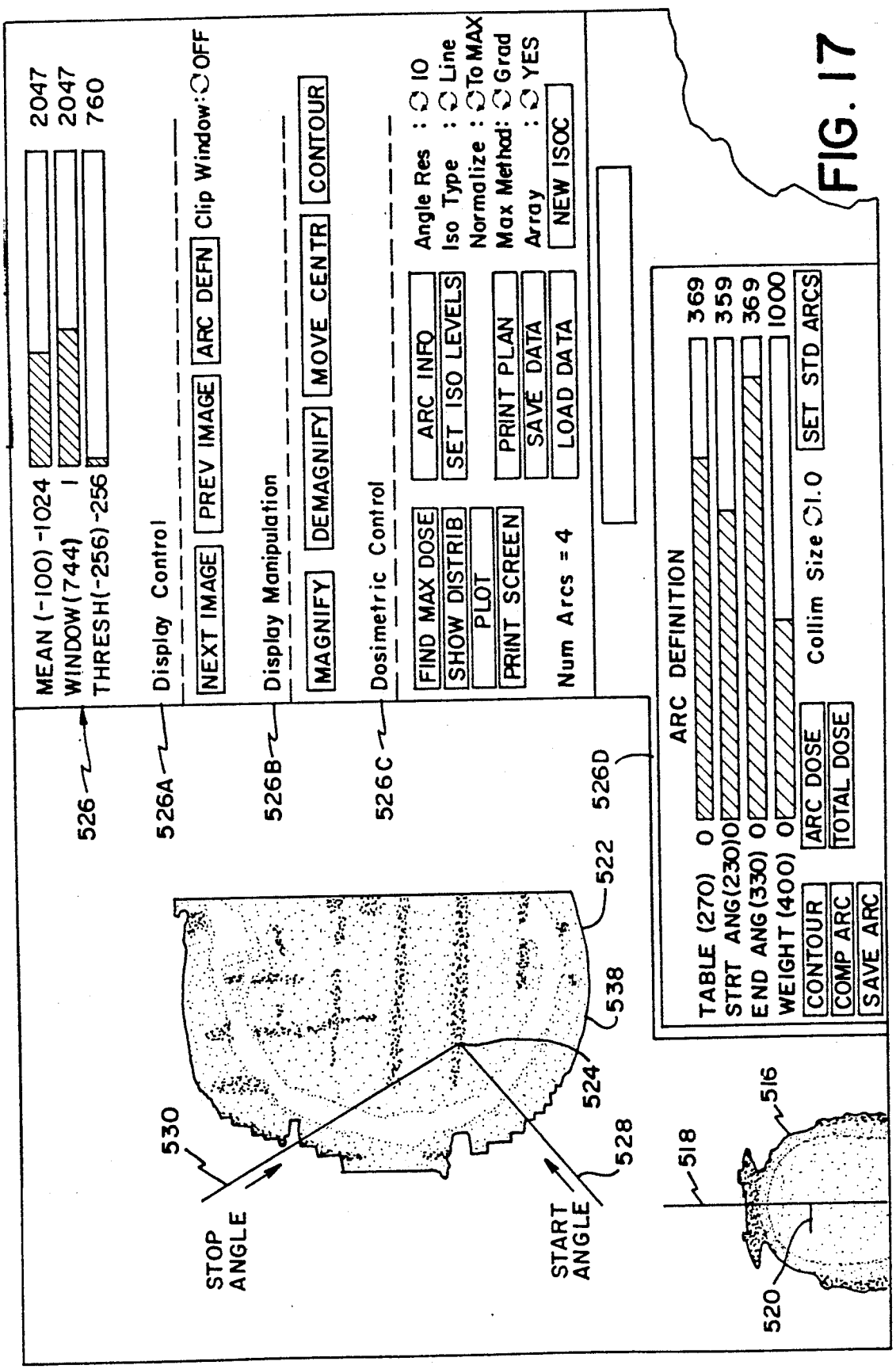
FIG. 17 is a view of the display produced during a portion of the present process.

Before discussing the further blocks of FIG. 16, reference is made to FIG. 17 which shows a view screen produced by the GAMMA program following the execution of block 514. Although FIG. 17 leaves out some minor portions for ease of illustration, the view screen of FIG. 17 includes a depiction of the patient's skull 516 having a view plane marker 518 disposed therein with a tick 520. The tick mark 520 shows where the isocenter of the target (not separately identified in image 516) is located. Since the view plane 518 is used to enter the plane for an arc through which the beam is moved, the plane 518 corresponds to the plane selected for the arc. (For ease of discussion, an "arc" will be discussed in terms of moving the radiation source, but it will be readily appreciated that the radiation source is moved for some arcs and the patient may be moved to implement other arcs such as moving the treatment table 20 of FIG. 3. It should also be appreciated that a more sophisticated might simultaneously move the radiation source and the patient.)

The image 516 is used to show the user or operator the orientation of an image 522. The image 522 is the CT slice along the view plane 518.

The image 522 shows an isocenter 524 which is within a target zone such as a tumor. The isocenter 524 may be selected by the doctor as a central location within the target or, alternately, could be selected automatically as a centroid within the target.

By use of the various control functions shown in portion 526 of the view screen of FIG. 17, one may define an arc within the proposed plan of treatment. The functions within portion 526 include display control functions located at 526A, display manipulation functions located at 526B, dosimetric control functions located at 526C, and arc definition functions located at 526D, all of these functions being defined in more detail with reference to the actual programs appended hereto and the summary of functions appended hereto. At any rate, the arc definition functions are used to define an arc for treatment. In particular, the start angle 528 and stop angle 530 as labeled on image 522 are shown. Additionally, other parameters such as the strength of the beam and the beam width may be input into the computer via 526D.

Referring back to FIG. 16, control transfers from block 514 to block 532 which causes the view plane 518 to be displayed on the screen or computer monitor as image 522 in FIG. 17. At the same time as displaying the view plane or image 522, block 532 simultaneously causes the computer to implement block 534 which creates a bit map of the pixels on the screen to the x,y,z coordinates of the patient reference coordinate system. In other words, a map is created showing the correspondence between each pixel of the image 522 and surrounding pixels and the coordinates set up by the CT scanner and previously transformed to BRW coordinates.

From blocks 532 and 534, control is transferred to block 536 whereat the outside contour of the patient is identified. In particular, the contour or outside edge 538 of the image 522 (FIG. 17) is detected by known edge detection techniques. Although not visible in the black and white reproduction of the view screen shown in FIG. 17, the program will then draw a yellow line corresponding to the outside edge or contour 538.

From block 536, control is transferred to block 540 whereat the user inputs the start angle corresponding to 528 in FIG. 17 and the stop or end angle corresponding to 530 in FIG. 17. After the user has selected the beginning and end of the arc, block 542 causes the storing of the beginning or start angle and the stop or ending angle.

From blocks 540 and 542, control is transferred to block 544 which draws a line between the source (i.e., the source at the particular location corresponding to a point on the arc) and the isocenter. Each of these lines is similar to lines 528 and 530 in FIG. 17 and these lines will be spaced one degree apart. Block 544 transfers control to block 546 which finds the intersection between each of the lines drawn in block 544 and the pixels corresponding to the contour or outer edge 538. Specifically, the computer starts at the isocenter 524 and proceeds along each of the lines, such as line 528 until it hits a pixel which is yellow. At the first pixel which is yellow, this represents the intersection between the line and the contour pixels. This intersection pixel represents the beam entrance point when the beam is in the direction extending along the line. For example, the beam entrance point for the beam at the start angle along line 528 is the intersection between line 528 and the contour 538. Such pixels corresponding to the beam entrance points are identified for every one degree starting at line 528 up to line 530. (Although FIG. 16 shows the block 544 drawing all the lines before the intersection is determined, the program may alternately draw one line at a time, find the intersection between the line and the contour pixels, and then loop back to draw another line, repeating the process until all of the intersection pixels have been identified.)

Control transfers from block 546 to block 548 which uses the previously established bit map in order to identify the x,y,z coordinate of the contour pixel which is intersected by the beam, this entrance point being identified in x,y,z coordinates for each such intersection pixel. From block 548, control transfer to block 550 whereat the beam entrance points are saved. These beam entrance points will be used later in the procedure in order to determine the dose at particular points within the patient.

After block 550, a decision block 552 tests to determine whether another arc is to be added as part of the treatment plan. Commonly, four such arcs would be used. Following entry of the first arc, the decision block 552 leads back to block 514 wherein the plane of the second arc may be entered and the process of FIG. 16 repeated.

Figure 18:
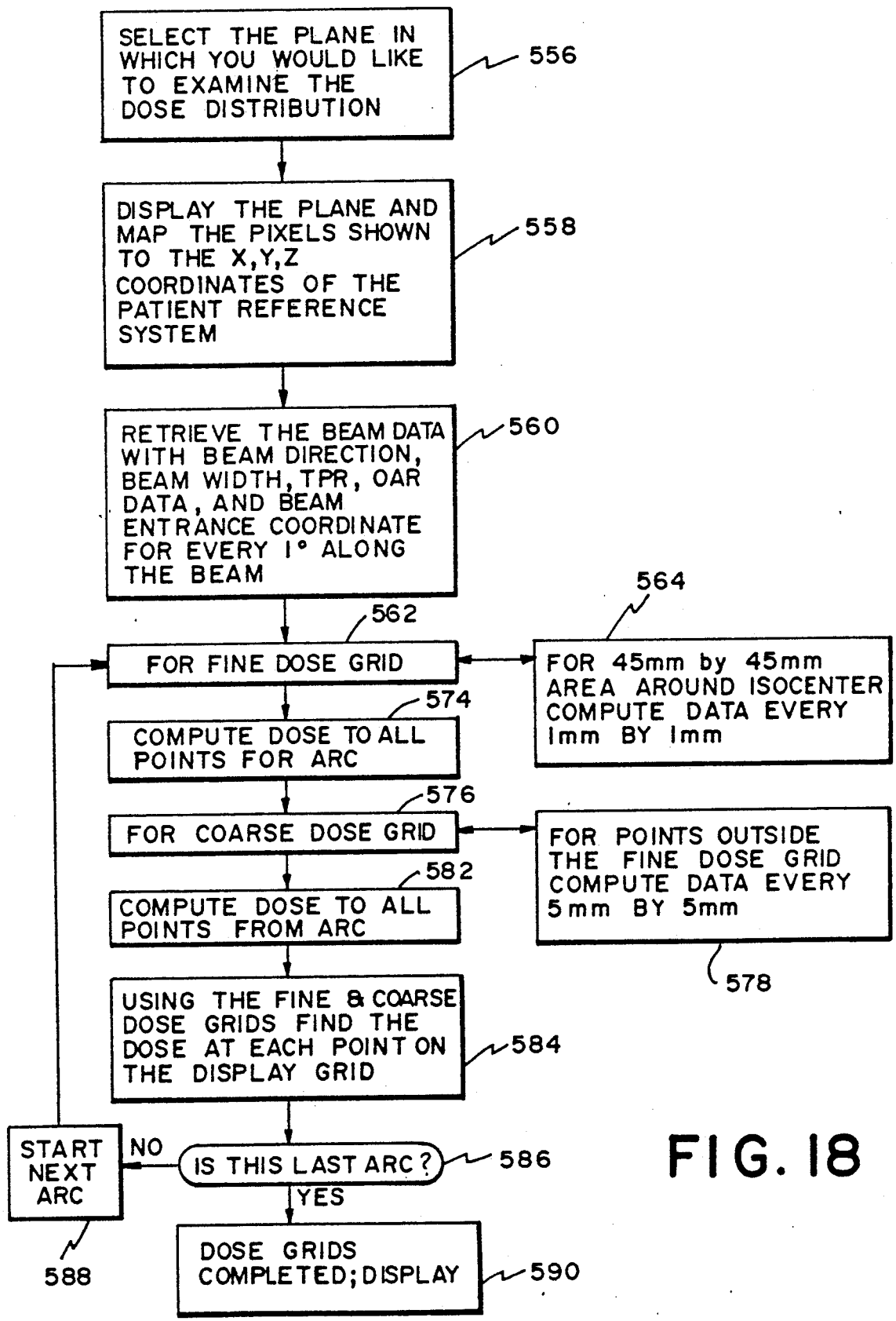
FIG. 18 is a simplified flow chart showing how the present process provides for displaying the radiation distribution in an arbitrarily selected plane.

Upon the decision block 552 indicating that no additional arcs are to be entered, block 552 transfers the control to the stop 554. As discussed above, the start and stop in FIG. 16 are illustrative and the process of FIG. 16 may be integrated into a much larger program, either as a portion of the program, or as a subroutine called thereby. With reference now to FIG. 18, the computing of a radiation dose from an arc to a selected viewing plane will be discussed. In other words, the doctor after entering the proposed plan of treatment, may arbitrarily select a plane in which he would like to examine the dose distribution. The doctor can examine the distribution resulting from a single arc or a group of arcs. The procedure of FIG. 18 would implemented by the program GAMMA (more specifically GAMMA2 although it is referred to herein as GAMMA) as is included in the appendix. At block 556, the doctor or other user selects the plane for which the dose distribution is desired. For example, the user can select a plane including a critical structure such as the optic nerve in order to determine if the dose distribution within the optic nerve is unacceptably high. The user will also want to insure that the dose distribution is adequate within the target adjacent to the isocenter. The user may select the plane by controlling and moving the view plane 518 in image 516 of FIG. 17. Known CT techniques and controls may be used to move a view plane such as 518, after which control transfers from block 556 to block 558 which will display the selected plane as an image such as 522 of FIG. 17. Additionally, block 558 maps the pixels shown in an image such as 522 to the x,y,z coordinates of the patient reference system. In other words, the computer sets up a correspondence between each pixel of the view plane image and the coordinates of the patient reference system which will have been previously established by the initial localization and imaging.

Following block 558, block 560 retrieves the stored beam data including the beam direction, beam width, TPR, OAR data and beam entrance coordinate for every one degree along the beam. In other words, the beam entrance points stored by the procedure of FIG. 16 will be retrieved and used for the process of FIG. 18. (The TPR and OAR relate to models for the intensity of the radiation beam and are discussed below in conjunction with FIG. 20A and 20B.

Figure 19:
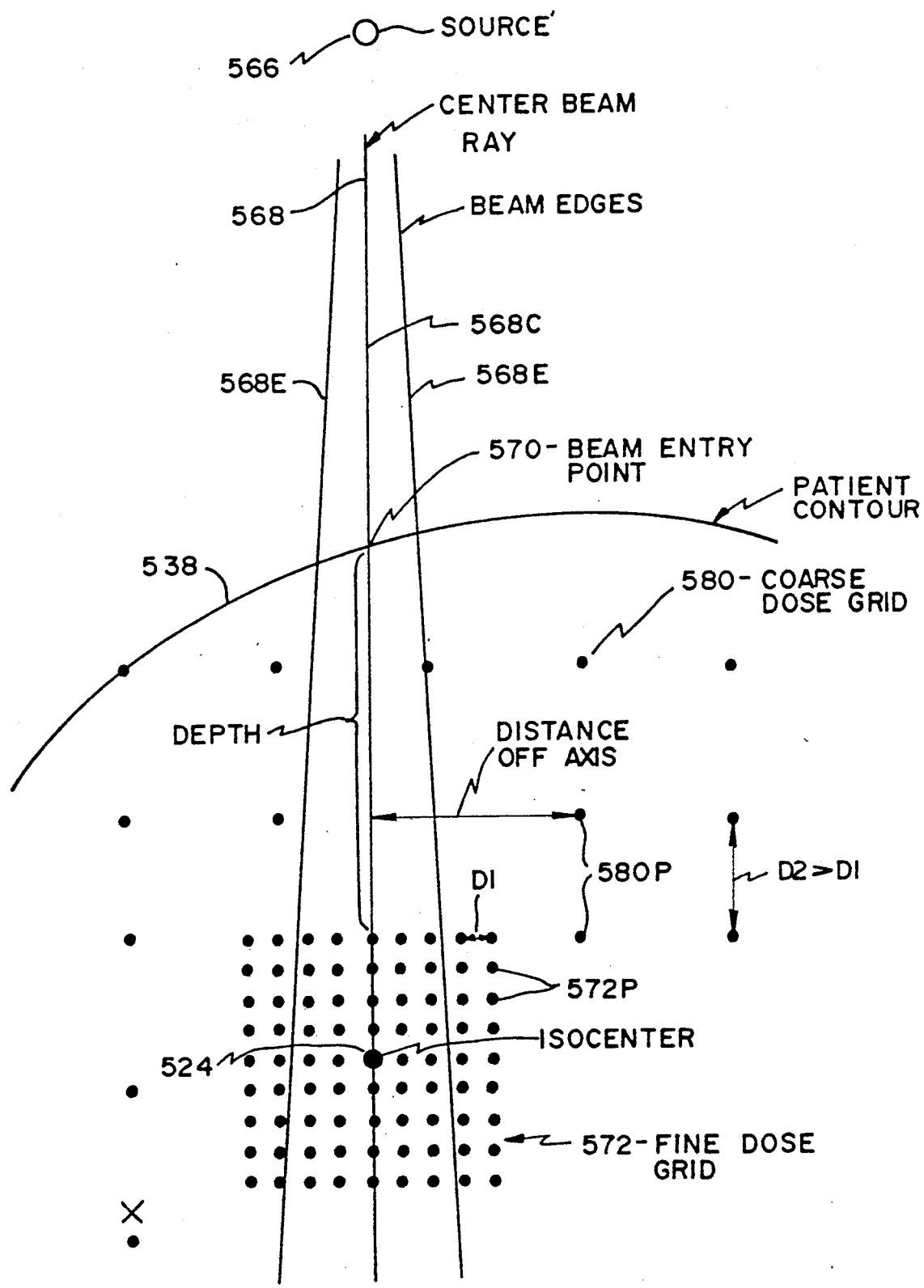
FIG. 19 is a simplified drawing showing a radiation beam entering a patient and illustrating several principles of operation of the present invention.

Block 560 leads to block 562 which establishes a fine dose grid around the isocenter, preferably a 45 mm by 45 mm area around the isocenter for which radiation dose data is computed every 1 mm. The establishment of the fine dose grid may be better understood with reference to FIG. 19 wherein a source 566 is shown to generate a radiation beam 568 having a center 568C and edges 568E. The center 568C enters the patient contour 538 on its way to isocenter 524 at a beam entry point 570. As illustrated in FIG. 19, a fine dose grid 572 is established in an area immediately around the isocenter 524. For the fine dose grid 572, the radiation dosage will be calculated at the points 572P spaced every 1 mm by 1 mm.

Returning to FIG. 18, blocks 562 and 564 lead to block 574 whereat the computer computes the dose to all points within the fine dose grid 572. The actual procedure for computing the dose for each point will be discussed in detail below. Block 574 leads to blocks 576 and 578 whereat a coarse dose grid is established for points outside the fine dose grid 572. The coarse dose grid 580 includes the points 580P in FIG. 19 which are outside the fine dose grid 572. The points 580P are spaced every 5 mm apart such that the density of points for which radiation dosage is calculated is significantly lower outside the fine dose grid than inside the fine dose grid.

Blocks 576 and 578 lead to block 582 whereat the dose for the points in the coarse dose grid 580 are calculated by procedures discussed in more detail below. Advantageously, the use of the fine dose grid 572 provides a high density of data points within an area adjacent to the isocenter, this area corresponding to a relatively high gradient for the radiation. At the same time, the use of a much lower density of data points for the coarse dose grid 580 allows one to reduce by over 90% the number of data points which must be used to provide the dosage for the arbitrarily selected viewing plane. In other words, the user will get a relatively complete picture for the selected plane without the requirement of tremendous time delays associated with calculating values for the numerous data points which would be required if the fine dose grid extended throughout the complete image. Since the gradient for the radiation is significantly lower in the area of the coarse dose grid, it is unnecessary to provide as high a density of data points in order to give the user the necessary information.

Following block 582, block 584 finds the dose for each point within the fine and coarse dose grids corresponding to the display, these points being illustrated as points 572P and 580P in FIG. 19. Block 584 leads to decision block 586 which tests to determine if all of the arcs have been included in the radiation dose computations. If not, block 586 leads to block 588 which starts the next arc returning to block 562. In other words, the contribution to each point on the dose grids may be separately calculated from each arc, although it will be appreciated that this could be handled a number of different ways provided that each point on the dose grids eventually takes into account the radiation contribution from each of the arcs. If block 586 indicates that the contributions from all of the arcs have been used for computing the fine and coarse dose grids, block 586 leads to block 590 which simply indicates that the dose grids have been completed and, if desired, may be displayed on the display, which display is a computer monitor also used for displaying the CT images.

Figure 21:
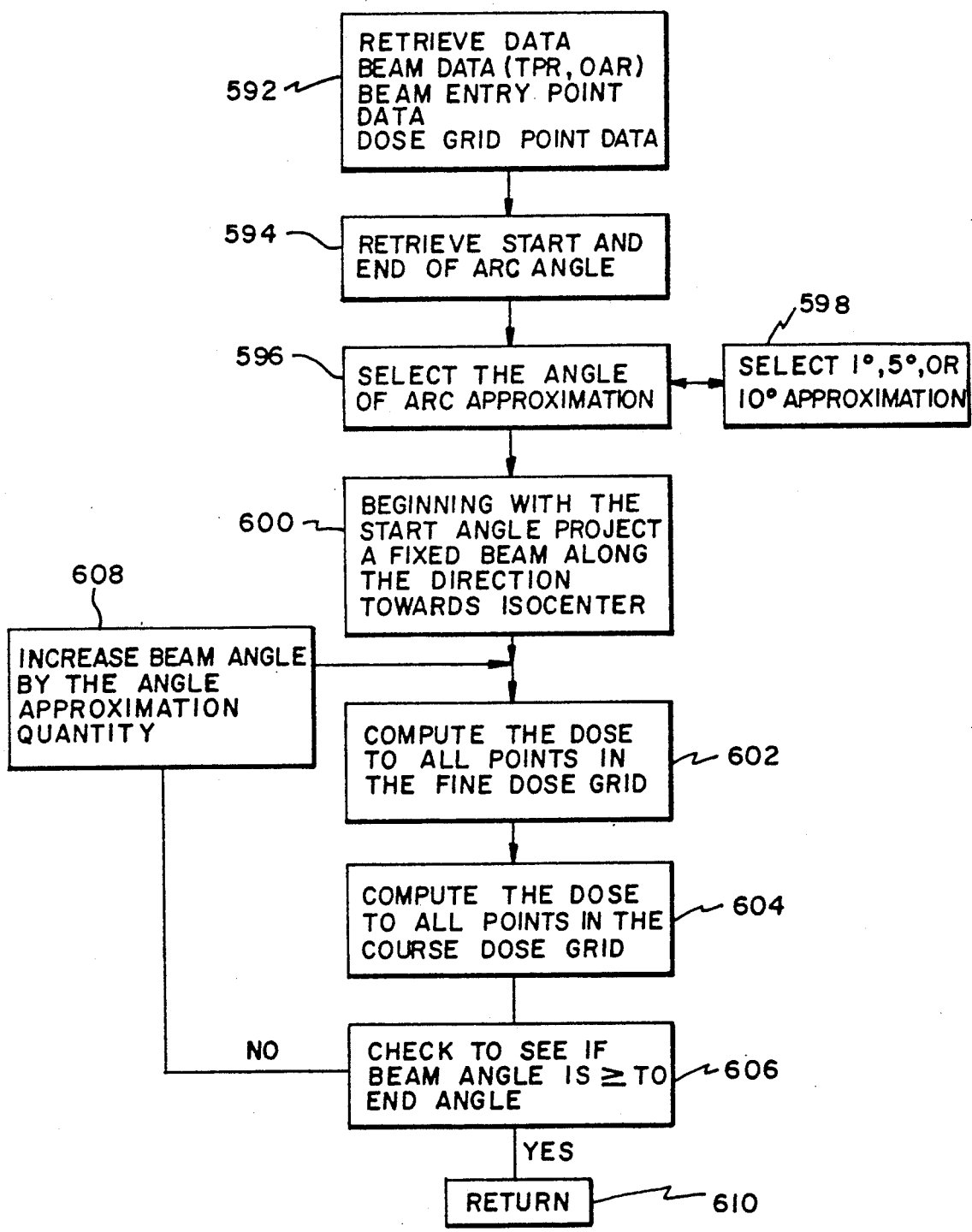
FIG. 21 is a simplified flow chart showing how the present process computes the radiation dose resulting from the radiation beam being swept through a particular arc.

In order to carry out the procedure of FIG. 18, a procedure is used to determine the radiation dose at each point within the dose grids as a result of a particular arc, this procedure being shown in detail as FIG. 21. In order to calculate the dose resulting from a particular arc, the procedure of FIG. 21 simulates the arc through which the radiation beam is swept by using calculations based on a series of stationary beams. The radiation contribution from each of the stationary beams is provided by the procedure shown in FIG. 22. Before discussing the detail procedure of FIGS. 21 and 22, reference will be made to FIGS. 20A and 20B. The intensity of a radiation beam may be modeled by the use of two parameters. The two parameters are the depth of tissue through which the beam has passed and the distance from the center line of the beam. The depth of tissue is called the tissue-phantom-ratio (TPR) while the distance from the beam center line is called the off-axis-ratio (OAR). To find the contribution of dose from a beam the two parameters must be known for each point in the dose grid. FIG. 20A shows how the intensity of the beam varies between the center of the beam and the beam edge, whereas FIG. 20B shows how the beam intensity varies with the depth of the beam within tissue. In order to find the contribution of dose from a particular beam, the two parameters, depth from the surface and distance from the center line of the beam, must be known and used in the computation. The depth of a particular point is shown in FIG. 19, whereas the distance off axis (i.e., distance from the beam center line) is shown in FIG. 19 for a different point.

Continuing to consider FIGS. 19, 20A and 20B, a model for the radiation beam 568 will be discussed. A model can be a simple measured data set of the radiation beam in a tissue-like material such as a data set obtained by measuring the beams energy (dose) deposition in water. It can also be a description of the radiation beam energy (dose) distribution obtained and mathematically modeled. In routine radiation treatment planning these models can be broken down into two broad groups. The first group comprises the more simple mathematical descriptions. These models take the radiation beam dose pattern and model it as a single entity. In other words, the model treats the beam as though the dose deposited from the radiation beam is all deposited in a pattern independent of the specific scattering caused by the specifics of the nearby tissue or bodily parts. A second, more sophisticated, group of beam models break the radiation down into primary radiation, i.e., the radiation which reaches a point inside the irradiated volume unattenuated by any of the overlying material, and scattered radiation which has resulted from the interaction of the primary radiation with overlying structures. Since this second type of radiation has been scattered it does not progress along the same directional path as the primary beam. When broad beams of radiation are used, as they are in routine external beam radiation therapy, this second component may account for up to 30% of the energy deposition of the beam. On the other hand, use of thin beams of radiation for stereotactic radio therapy has generally not been practical because of the problems obtaining the required degree of accuracy for the bearing systems used to position the radiation source and patient relative to each other. In other words, the mechanical structures have more than a certain degree of inaccuracy built into them and the beam must be large enough in width such that the beam will hit the desired target, even if the mechanical inaccuracy causes the center of the beam to shift from the desired position.

The mechanical structures discussed with reference to FIGS. 3-14 provide sufficient accuracy that the present invention can use "pencil beams" for patient treatment. These pencil beams, should be less than 5 centimeters in width or diameter and, more preferably below 3 centimeters in width or diameter. Use of such thin beams is advantageous in that a simpler mathematical model may be used which does not require specific calculations for the scattered component separately from the main beam.

A model for simple beams which has been used for some time in the field of treatment planning is the tissue phantom ration (TMR) model coupled with the off axis ratio (OAR) model. These models are mathematically very simple and correspond respectively to FIGS. 20A and 20B. To further increase the speed of the present technique, the computer system includes large look-up tables of the tabulated beam data which are prepared in advance. This allows the system to simply look up the tabular value for either TMR or OAR as a patient dose distribution is being computed. As these values have been computed in advance, the computations necessary for any individual case is kept to a minimum.

The small beam size used in the present technique allows a very common computation to be neglected with no significant loss in accuracy. This is the correction for oblique filtration. The dose distributions which are computed for routine teletherapy beams are done so on a flat surface phantom. When the beams are applied to an individual patient, very often the surface of the patient through which the beam enters is not flat. It may be curved or it may be straight but oblique to the beam. The perturbation created by such a change in surface contour causes major changes in the energy distribution below the surface. However, by use of the small diameter or small width beams, the patients head curves only very slightly over the small width or diameter of the beam. Therefore, taking into account the curvature of the patient's head would not significantly modify the results. The present invention therefore ignores the correction and this allows for very rapid dose computation for two reasons. The first savings in computational expense comes from the simple reduction in the number of calculations which can be left out when computing the dose distribution from each beam. The second savings in computational time, which is more substantial, comes from not having to locate more than one entry point per beam. In order to compute the correction for the oblique filtration, the surface contour must be found. This is routinely done by first obtaining multiple contours of the patient head. Once this is done, the surface of the head is tiled. The intersection of the beam with the tiled surface must be found. This process is very time consuming. By being able to simply find the single point through which the beam center enters the patient and ignoring the rest of the surface for each beam, a very quick process may be used to calculate radiation dose distributions.

From the above, it will be appreciated that the patient's head appears flat relative to a small diameter or width beam such that edge effects (the fact that the edge of beam enters the patient contour 538 at a slightly different angle than the center 568C of the beam. It should be noted that FIG. 19 may be considered as somewhat exaggerating the spreading of the beam. In other words, the edges 568E will be almost parallel to the center 568C.

Turning now to FIG. 21, the technique for computing the dose to all points in the grid from a particular arc will be explained. At block 592, the beam data (TPR) (OAR), beam entrance point data and dose grid point data (i.e., x,y,z coordinates of the pixels corresponding the fine dose grid points 572P and pixels corresponding to the coarse dose grids points 580P) are retrieved. Control transfer to block 594 whereat the start and stop or end of the arc angle is provided. The angle of arc approximation may be set by the operator at blocks 596 and 598. In particular, the arc through which the source is swept (or the patient swept relative to the source) may be simulated by a series of stationary beams every one degree, every five degrees, or every ten degrees. In other words, if the arc swept through 100 degrees, and the operator selects ten degrees as the increment for the approximation, the arc or swept beam may be simulated by ten stationary beams, one located every ten degrees.

Following blocks 596 and 598, the block 600 starts with the art angle and projects a fixed beam along the direction towards the isocenter. In other words, it draws in a beam corresponding to the stationary beam which approximates the swept beam. Block 600 leads to block 602 which computes the dose to all points in the fine dose grid resulting from the stationary beam. Block 602 leads to block 604 which computes the dose to all points in the coarse dose grid resulting from this single stationary beam. In making the computation of blocks 602 and 604 a procedure discussed in more detail with respect to FIG. 22 will be utilized.

Block 604 transfers control to block 606 which determines if the beam angle is greater than or equal to the end angle. In other words, has the computer taken into account all of the stationary beams which are used to model or simulate the swept beam. In the example where the arc will be 100 degrees, and a stationary beam is used every ten degrees, the arc will be simulated by ten stationary beams. Block 606 will transfer control to block 608 as long as the stationary beam which is under consideration is not yet the final beam. Block 608 increases the beam angle by the approximation quantity. For example, with the 100 degree arc situation discussed above, and assuming that the angle is initially zero degrees, block 608 will add ten degrees to the direction and return control to block 602 which will now compute the dose corresponding to a beam having a direction of ten degrees. Blocks 602 and 604 will repeat this for beams having directions of 20 degrees, 30 degrees, up to 100 degrees whereupon block 606 will transfer control to block 610 which is a return. That stage, the procedure will have computed the dose at the points on the dose grids which result from a particular arc. This information is used by the procedure of FIG. 16 and the procedure of FIG. 21 would be repeated for each of the arcs.

Figure 22:
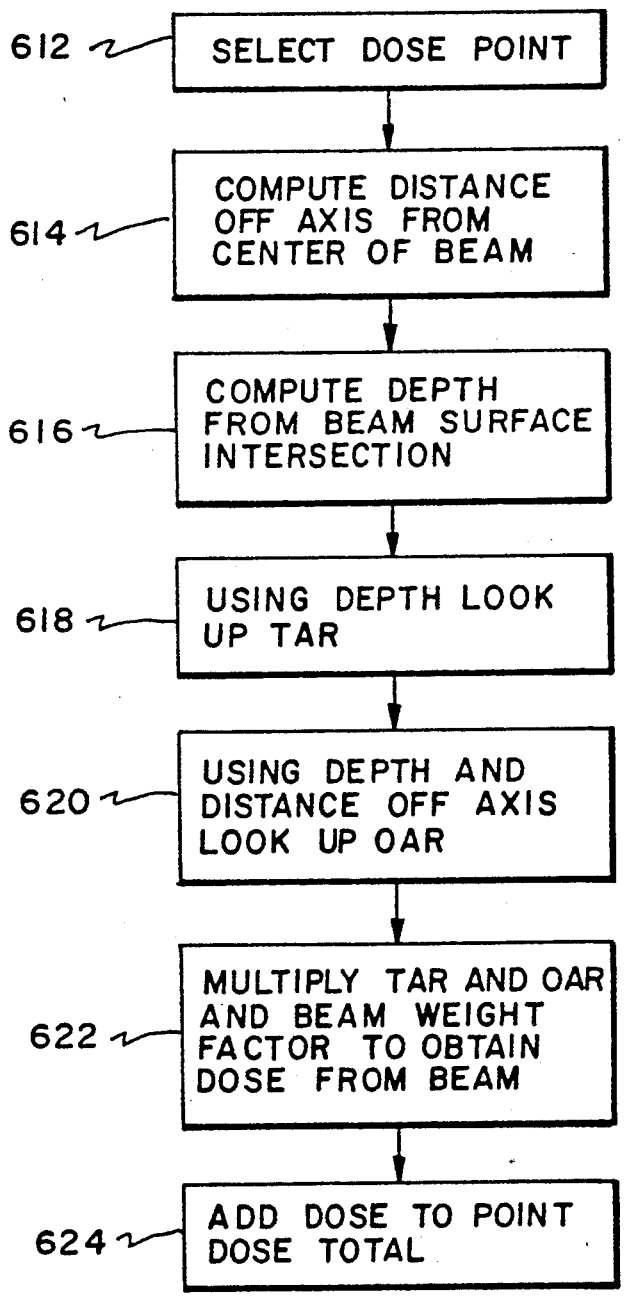
FIG. 22 is a simplified flow chart illustrating the computation of the radiation dose at a particular point from a beam.

FIG. 22 shows how the procedures of FIGS. 18 and 21 utilize a process to determine the dose at any particular point which is within the fine dose grid or the coarse dose grid. Initially block 612 involves the selection of the dose point. In other words, which of the points corresponding 572P or 580P is under consideration. As will be readily appreciated the procedure of FIG. 22 will be repeated for each of the points in the dose grids 572 and 580.

Following block 612, block 614 computes the distance off axis from the center line of the beam. Next, block 616 computes the depth of the particular dose point from the beam-surface intersection. Control then transfers to block 618 whereat the computer uses the depth to access a look up table having data points corresponding to FIG. 20B stored therein. At block 620, the depth and the distance off axis are used to look up a table having data points corresponding to FIG. 20A.

Next, block 622 uses the values which were looked up for calculating the dose at the particular point. In particular, the values which were looked up are multiplied by the beam weight factor to obtain the dose at the particular dose grid point resulting from the particular stationary beam. Control then transfer to block 624 which keeps a running sum of the dose at a particular point. Block 24 adds the dose from the given stationary beam to any previously stored doses for that point. For each stationary beam simulating an arc, the contribution of that beam to each point will be calculated by repeatedly going through the steps of FIG. 22.

Figure 23:
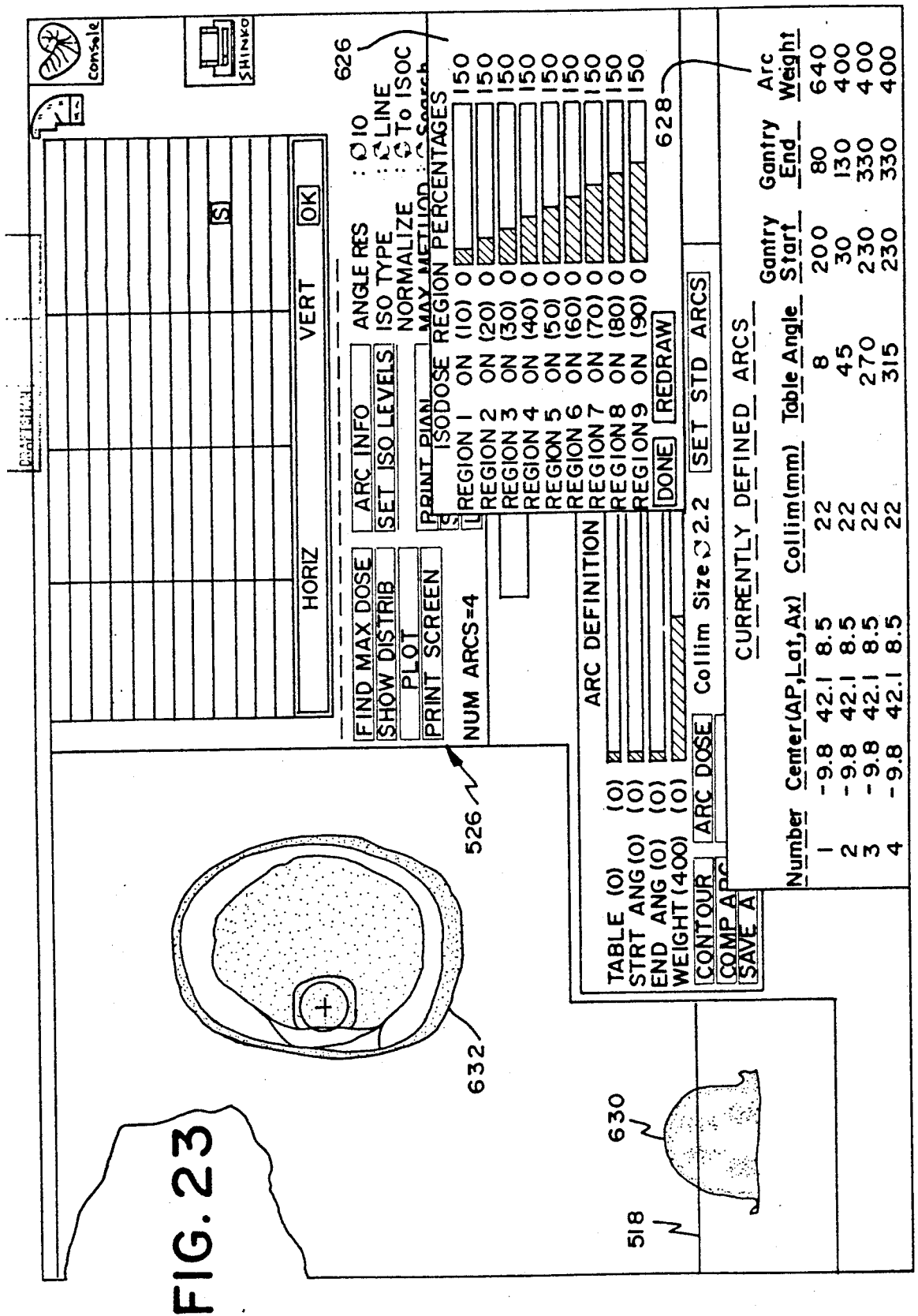
FIG. 23 shows a view screen produced by the process of the present invention.

FIG. 23 shows the view on the display or computer monitor during a portion of the GAMMA program. In particular, the instructions section 526 includes a number of windows appearing thereon. For example, window 626 illustrates the isodose region percentages whereas window 628 shows the currently defined arcs. The screen also includes the orientation image 630 showing the view plane 518. The view plane 518 shows the plane for the cross sectional image shown at 632. The image 632 is the CT image or slice and includes radiation distribution data superimposed thereon as will be discussed in more detail below.

Figure 24:
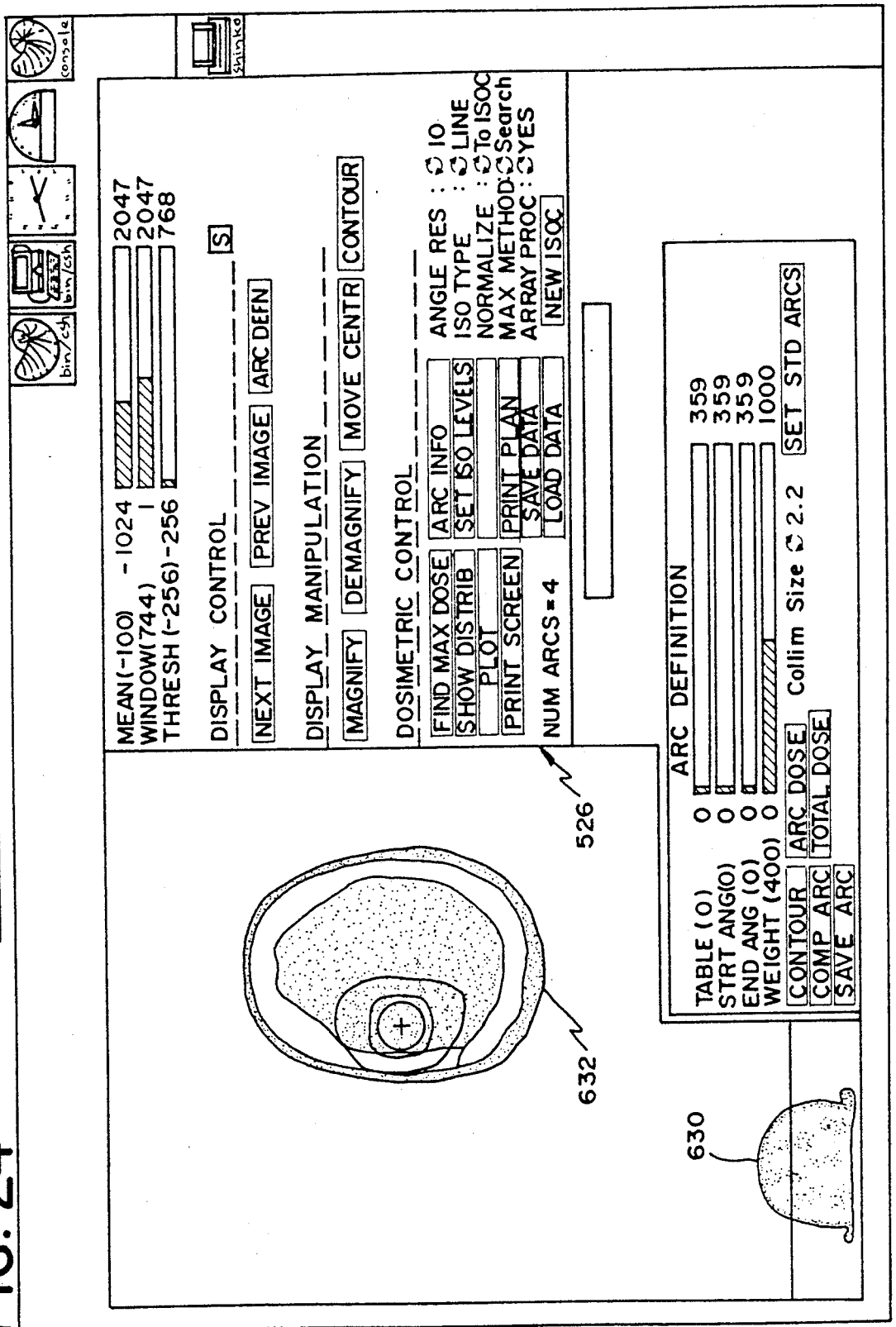
FIG. 24 shows a view screen as produced without any windows.

Referring now to FIG. 24, this shows the view on the screen or display corresponding to the GAMMA program without any windows. As with the other view screens, this is generated by the programs attached as an appendix hereto which programs are in the C language.

FIG. 25 shows a simplified view of the image 632 of FIGS. 23 and 24. In particular, the image 632 shows the isocenter 634 and a series of isodose lines 636 extending about the isocenter. The isodose lines correspond to different percentages of the radiation dosage. In other words, if the isocenter is considered to receive 100% of the dose, the innermost isodose line might receive 90%, the next isodose line might receive 80% and so forth. For ease of illustration, only two of the isodose lines 636 have been included. The isodose lines may be computed by determining the radiation doses at the dose and grid points (not separately shown in FIG. 25 refer back to FIG. 19), the program generates the isodose lines 636 and displays them on the CT image 632.

Figure 26:
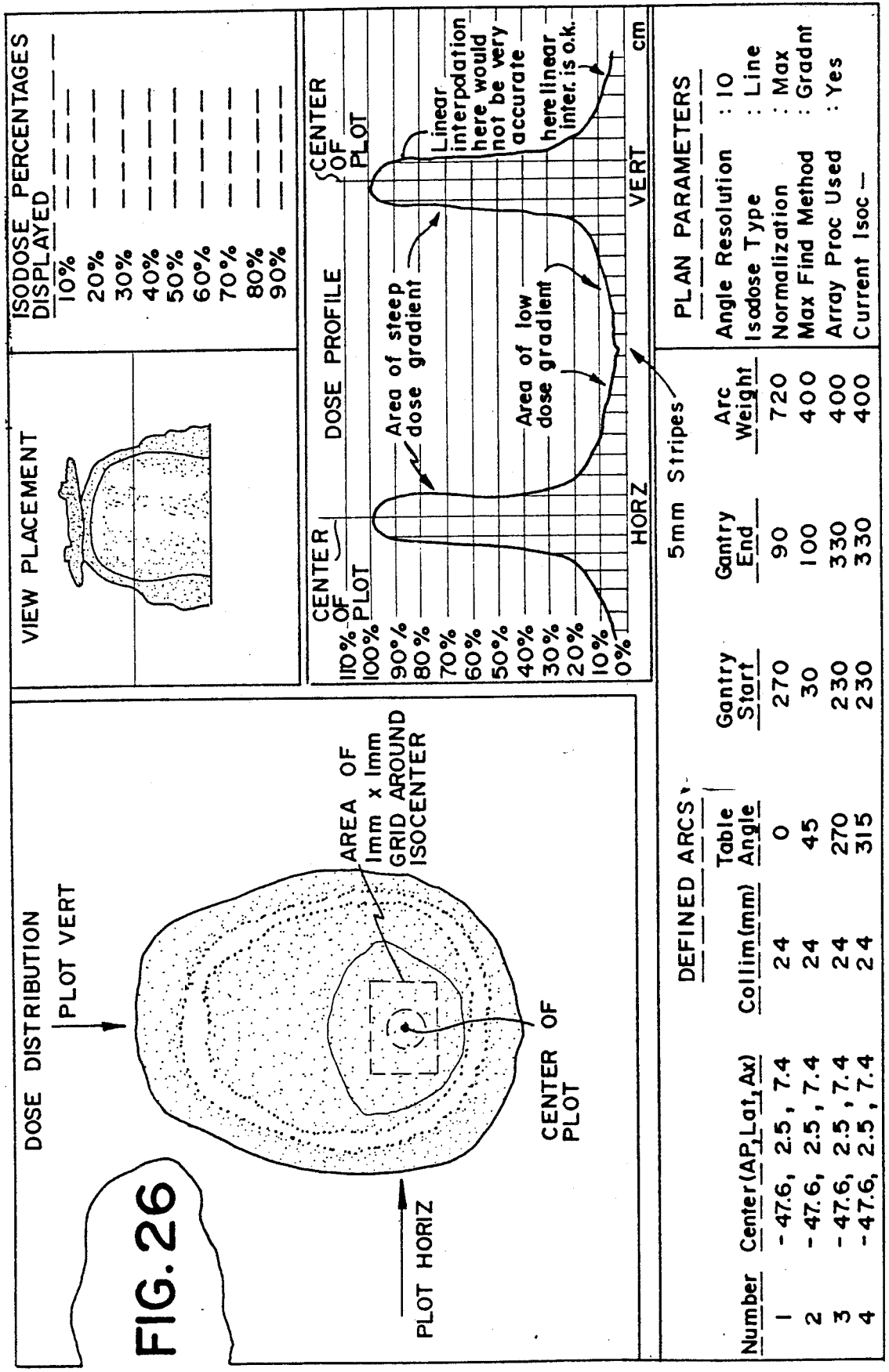
FIG. 26 shows a view screen produced by the present invention wherein the vertical and horizontal distributions of radiation are plotted.

With reference now to FIG. 26, there is shown the screen contents when the user has requested the horizontal and vertical distribution of the radiation. The distribution plots at the right of FIG. 26 illustrate how the distribution gradient is relatively high adjacent to the isocenter and is relatively low somewhat further away from the isocenter. Accordingly, the fine dose grid calculates doses at a relatively high density of points in the area where the radiation gradient is high and calculates the radiation doses at a relatively low density of points in the coarse dose grid where the radiation gradient is relatively low.

FIG. 27 is a simplified view of the overall system which may be used in conjunction with the discussed procedures. In particular, the procedure may be implemented using a CT scanner 650 which gets patient reference data, although other arrangements might be used, the reference data may be written onto magnetic tape in a tape drive 652 for transfer to computer CPU 654, which may be a Sun 4/280. Instead of using the CT scanner, a nuclear magnetic resonance imaging system 656 might be used to supply data to the tape drive 652.

X-rays produced from the angiographic procedure represented by block 658 may be digitized by block 660 for transfer to the computer 654. A monitor 662 is connected to the computer 654 and is used to display the various screen images discussed above. Additionally, by use of a mouse and the various illustrated controls on the view screens, the monitor 662 may be used for operator input/output to the computer 654. Although not separately illustrated, a printer could be connected to the computer 654 to print any of the data calculated therein. For example, the printer could be used to print the screen and such a command was used to generate several of the view screens which are discussed above.

While the foregoing has described a preferred embodiment of the system, it will be appreciated by those skilled in the art that variations may be made without departing from the principles and spirit of the invention, the scope of which is defined in the appended claims.

What is claimed is:

1. A method for patient care comprising the steps of:
   (a) localizing a target within a patient;
   (b) subjecting the patient to an imaging system with a display to generate patient reference data in the form of x,y,z coordinates of the target and adjacent portions of the patient;
   (c) supplying the patient reference data to a dosimetric computer connected to said display;
   (d) inputting into the dosimetric computer a proposed plan for applying at least one beam of radiation to the patient from at least one source and from at least two different directions;
   (e) selecting a plane of the patient for display of a distribution of radiation which would result from the proposed plan;
   (f) displaying on said display a selected plane patient image corresponding to the selected plane by operation of the imaging system;
   (g) determining the distribution of radiation within the selected plane by calculating the radiation dose at points spaced by distance D1 within a fine dose grid relatively close to the target and calculating the radiation dose at points spaced by distance D2, greater than D1, within a coarse dose grid outside said fine dose grid, the dosimetric computer performing the calculations for the radiation dose at a greater density of points in the fine dose grid and at a lower density of points in the coarse dose grid; and (h) displaying data on the display from the radiation dose calculations.

2. The method of claim 1 wherein some data resulting from the radiation dose calculations is placed on the patient image in the display.

3. The method of claim 2 wherein the proposed plan includes at least a first arc through which the beam is applied to the patient, said first arc being in a first arc plane, and wherein said inputting step includes the substeps of:
selecting the first arc plane; displaying a first arc plane patient image corresponding to the first arc plane on the display;
creating a bit map of pixels on the display to said x,y,z coordinates of the patient reference data;
identifying each pixel which makes up an outside contour of the patient;
storing the beginning and end of the first arc;
drawing a line between the source at a given location and an isocenter within the target;
finding the intersection pixel of the line and the pixels corresponding to the outside contour;
referencing the bit map to identify the x,y,z coordinates of the intersection pixel as a beam entrance point;
repeating the drawing, finding, and referencing substeps to identify additional beam entrance points corresponding to different source locations; and
storing the beam entrance points, these beam entrance points corresponding to the center of the beam at different source locations.

4. The method of claim 3 wherein the stored beam entrance points are used to perform the radiation dose calculations.

5. The method of claim 4 wherein the radiation dose calculations are performed for each of said different source locations based on radiation entering only at said beam entrance points such that edge effects are ignored.

6. The method of claim 5 wherein the width of each beam used in the proposed plan is less than 5 cm such that ignoring edge effects will not introduce substantial errors.

7. The method of claim 6 further comprising the step of:
subjecting the patient to radiation in accord with the proposed plan.

8. The method of claim 4 further comprising the step of:
subjecting the patient to radiation in accord with the proposed plan.

9. The method of claim 1 further comprising the step of:
subjecting the patient to radiation in accord with the proposed plan.

10. A method for patient care comprising the steps of:
(a) localizing a target within a patient;
(b) subjecting the patient to an imaging system with a display to generate patient reference data in the form of x,y,z coordinates of the target and adjacent portions of the patient;
(c) supplying the patient reference data to a dosimetric computer connected to said display;
(d) inputting into the dosimetric computer a proposed plan for applying at least one beam of radiation to the patient from at least one source and from at least two different directions;
wherein the proposed plan includes at least a first arc through which the beam is applied to the patient, said first arc being in a first arc plane, and wherein said inputting step includes the substeps of:
selecting the first arc plane;
displaying a first arc plane patient image corresponding to the first arc plane on the display;
creating a bit map of pixels on the display to said x,y,z coordinates of the patient reference data;
identifying each pixel which makes up an outside contour of the patient;
storing the beginning and end of the first arc;
drawing a line between the source at a given location and an isocenter within the target;
finding the intersection pixel of the line and the pixels corresponding to the outside contour;
referencing the bit map to identify the x,y,z coordinates of the intersection pixel as a beam entrance point;
repeating the drawing, finding, and referencing substeps to identify additional beam entrance points corresponding to different source locations; and
storing the beam entrance points, these beam entrance points corresponding to the center of the beam at different source locations.

11. The method of claim 10 further comprising:
selecting a plane of the patient for display of a distribution of radiation which would result from the proposed plan;
displaying on said display a selected phase patient image corresponding to the selected plane by operation of the imaging system;
determining the distribution of radiation within the selected plane; and displaying data on the display resulting from the distribution determination.

12. The method of claim 11 wherein the determination of the distribution is accomplished by calculating the radiation dose at points spaced by distance D1 within a fine dose grid relatively close to the target and calculating the radiation dose at points spaced by distance D2, greater than D1 within a coarse dose grid outside said fine dose grid; the dosimetric computer performing the calculations for the radiation dose at a greater density of points in the fine dose grid and at a lower density of points in the coarse does grid.

13. The method of claim 12 wherein the stored beam entrance points are used to perform the radiation dose calculations.

14. The method of claim 13 wherein the radiation dose calculations are performed for each of said different source locations based on radiation entering only at said beam entrance points such that edge effects are ignored.

15. The method of claim 14 further comprising the step of:
subjecting the patient to radiation in accord with the proposed plan.

16. The method of claim 15 wherein the beam or beams applied to the patient are less than 5 cm in width.

17. The method of claim 10 further comprising the step of:
subjecting the patient to radiation in accord with the proposed plan.

18. The method of claim 17 wherein the beam or beams applied to the patient are less than 5 cm in width.

19. A method for patient care comprising the steps of:
(a) localizing a target within a patient;
(b) subjecting the patient to an imaging system with a display to generate patient reference data in the form of x,y,z coordinates of the target and adjacent portions of the patient;

(c) supplying the patient reference data to a dosimetric computer connected to said display;

(d) inputting into the dosimetric computer a proposed plan for applying at least one beam of radiation to the patient from at least one source and from at least two different directions;

(e) selecting a plane of the patient for display of a distribution of radiation which would result from the proposed plan;

(f) displaying on said display a patient image corresponding to the selected plane by operation of the imaging system;

(g) determining the distribution of radiation within the selected plane by calculating the radiation dose at points spaced by distance D1 within a fine dose grid relatively close to the target and calculating the radiation dose at points spaced by distance D2, greater than D1, within a coarse dose grid outside said fine dose grid, the dosimetric computer performing the calculations for the radiation dose at a greater density of points in the fine dose grid and at a lower density of points in the coarse dose grid; and (h) outputting data from the radiation dose calculations.

20. The method of claim 19 further comprising the step of subjecting the patient to radiation in accord with the proposed plan using a stereotactic radiosurgery apparatus comprising:

a gantry supported for rotation about a gantry axis, the gantry having a radiation-emitting head for movement in an arc in a radiation plane about a center point corresponding to an intersection of the gantry axis and the radiation plane, said gantry axis being normal to said radiation plane;

a collimator disposed to focus radiation from said radiation-emitting head on said center point; and collimator linking means for linking movement of said collimator to said radiation-emitting head for automatic rotation of said collimator in said radiation plane and about said gantry axis upon rotation of said gantry, said collimator linking means allowing said collimator to track rotation of said gantry with no or minimal transfer of positioning inaccuracies from said gantry to said collimator.

* * * * *